(12) United States Patent
Chang et al.

(10) Patent No.: US 11,554,012 B2
(45) Date of Patent: Jan. 17, 2023

(54) VALVE HOLDER ASSEMBLY WITH SUTURE LOOPING PROTECTION

(71) Applicant: Edwards Lifesciences Corporation, Irvine, CA (US)

(72) Inventors: Da-Yu Chang, Irvine, CA (US); Amy E. Munnelly, Irvine, CA (US); Van Huynh, Anaheim, CA (US); Avina Gupta, Alta Loma, CA (US); Brian S. Conklin, Orange, CA (US); Sooji Van Echten, Cerritos, CA (US); Kurt Kelly Reed, Huntington Beach, CA (US); Amanda Grace Sall, Hoover, AL (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 17/806,928

(22) Filed: Jun. 14, 2022

(65) Prior Publication Data

US 2022/0313429 A1 Oct. 6, 2022

Related U.S. Application Data

(63) Continuation of application No. PCT/US2020/064895, filed on Dec. 14, 2020.
(Continued)

(51) Int. Cl.
*A61F 2/24* (2006.01)

(52) U.S. Cl.
CPC .......... *A61F 2/2427* (2013.01); *A61F 2/2409* (2013.01); *A61F 2/2412* (2013.01); *A61F 2/2418* (2013.01); *A61F 2220/0075* (2013.01)

(58) Field of Classification Search
CPC .... A61F 2/2409; A61F 2/2412; A61F 2/2418; A61F 2/2427
See application file for complete search history.

(56) References Cited

U.S. PATENT DOCUMENTS

| 3,143,742 A | 8/1964 | Cromie |
| 3,320,972 A | 5/1967 | High et al. |

(Continued)

FOREIGN PATENT DOCUMENTS

| CN | 104523353 A | 4/2015 |
| EP | 0125393 A1 | 11/1984 |

(Continued)

OTHER PUBLICATIONS

"Minimally Invasive Mitral Valve Surgery," Navia, Dept of Thoracic and CardioThoracic Surgery, The Cleveland Clinic Foundation, Cleveland, OH.

(Continued)

*Primary Examiner* — Suba Ganesan
(74) *Attorney, Agent, or Firm* — Guy Cumberbatch

(57) ABSTRACT

A prosthetic heart valve has a plurality of valve leaflets that control directional flow of blood through a heart and a stent structure having a plurality of commissure posts supporting the valve leaflets. The stent structure has a covering over the plurality of commissure posts and has a sewing ring at an inflow end of the stent structure. Each of the plurality of commissure posts has a tip and a suture loop is attached to the covering at a location adjacent to or on the tip of the commissure post. Each suture loop provides a passage for a suture to pass through between the covering and the suture loop.

20 Claims, 30 Drawing Sheets

Related U.S. Application Data

(60) Provisional application No. 62/948,744, filed on Dec. 16, 2019.

(56) References Cited

U.S. PATENT DOCUMENTS

| | | | |
|---|---|---|---|
| 3,371,352 A | 3/1968 | Siposs et al. |
| 3,546,710 A | 12/1970 | Shumakov et al. |
| 3,574,865 A | 4/1971 | Hamaker |
| 3,656,185 A | 4/1972 | Carpentier |
| 3,755,823 A | 9/1973 | Hancock |
| 3,839,741 A | 10/1974 | Haller |
| 3,997,923 A | 12/1976 | Possis |
| 4,035,849 A | 7/1977 | Angell et al. |
| 4,079,468 A | 3/1978 | Liotta et al. |
| 4,084,268 A | 4/1978 | Ionescu et al. |
| 4,106,129 A | 8/1978 | Carpentier et al. |
| 4,164,046 A | 8/1979 | Cooley |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| RE30,912 E | 4/1982 | Hancock |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,602,911 A | 7/1986 | Ahmadi et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,041,130 A | 8/1991 | Cosgrove et al. |
| 5,061,277 A | 10/1991 | Carpentier et al. |
| 5,064,431 A | 11/1991 | Gilbertson et al. |
| 5,104,407 A | 4/1992 | Lam et al. |
| 5,147,391 A | 9/1992 | Lane |
| 5,163,955 A | 11/1992 | Love et al. |
| 5,201,880 A | 4/1993 | Wright et al. |
| 5,258,021 A | 11/1993 | Duran |
| 5,258,023 A | 11/1993 | Reger |
| 5,306,296 A | 4/1994 | Wright et al. |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,496,336 A | 3/1996 | Cosgrove et al. |
| 5,500,016 A | 3/1996 | Fisher |
| 5,533,515 A | 7/1996 | Coller et al. |
| D372,781 S | 8/1996 | Reif |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,593,435 A | 1/1997 | Carpentier et al. |
| 5,607,471 A | 3/1997 | Seguin et al. |
| 5,618,307 A | 4/1997 | Donlon et al. |
| 5,626,607 A | 5/1997 | Malecki et al. |
| 5,628,789 A | 5/1997 | Vanney et al. |
| 5,674,279 A | 10/1997 | Wright et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,189 A | 7/1998 | Khalid |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,066 A | 10/1998 | Gross |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,888,240 A | 3/1999 | Carpentier et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,972,030 A | 10/1999 | Garrison et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,102,945 A | 8/2000 | Campbell |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,143,024 A | 11/2000 | Campbell et al. |
| 6,159,240 A | 12/2000 | Sparer et al. |
| 6,162,233 A | 12/2000 | Williamson, IV et al. |
| 6,168,614 B1 | 1/2001 | Andersen et al. |

(56) References Cited

U.S. PATENT DOCUMENTS

| | | |
|---|---|---|
| 6,176,877 B1 | 1/2001 | Buchanan et al. |
| 6,183,512 B1 | 2/2001 | Howanec, Jr. et al. |
| 6,187,040 B1 | 2/2001 | Wright |
| 6,197,054 B1 | 3/2001 | Hamblin, Jr. et al. |
| 6,217,610 B1 | 4/2001 | Carpentier et al. |
| 6,217,611 B1 | 4/2001 | Klostermeyer |
| 6,231,561 B1 | 5/2001 | Frazier et al. |
| 6,231,602 B1 | 5/2001 | Carpentier et al. |
| 6,241,765 B1 | 6/2001 | Griffin et al. |
| 6,245,102 B1 | 6/2001 | Jayaraman |
| 6,250,308 B1 | 6/2001 | Cox |
| 6,258,122 B1 | 7/2001 | Tweden et al. |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,319,280 B1 | 11/2001 | Schoon |
| 6,328,727 B1 | 12/2001 | Frazier et al. |
| 6,332,893 B1 | 12/2001 | Mortier et al. |
| 6,350,282 B1 | 2/2002 | Eberhardt |
| 6,371,983 B1 | 4/2002 | Lane |
| 6,375,620 B1 | 4/2002 | Oser et al. |
| 6,391,054 B2 | 5/2002 | Carpentier et al. |
| 6,402,780 B2 | 6/2002 | Williamson, IV et al. |
| 6,406,493 B1 | 6/2002 | Tu et al. |
| 6,409,674 B1 | 6/2002 | Brockway et al. |
| 6,419,698 B1 | 7/2002 | Finger |
| 6,425,916 B1 | 7/2002 | Garrison et al. |
| 6,440,164 B1 | 8/2002 | DiMatteo et al. |
| 6,442,413 B1 | 8/2002 | Silver |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,602,288 B1 | 8/2003 | Cosgrove et al. |
| 6,602,289 B1 | 8/2003 | Colvin et al. |
| 6,619,291 B2 | 9/2003 | Hlavka et al. |
| 6,645,143 B2 | 11/2003 | VanTassel et al. |
| 6,652,464 B2 | 11/2003 | Schwartz et al. |
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |
| 6,709,456 B2 | 3/2004 | Langberg et al. |
| 6,718,985 B2 | 4/2004 | Hlavka et al. |
| 6,719,786 B2 | 4/2004 | Ryan et al. |
| 6,726,717 B2 | 4/2004 | Alfieri et al. |
| 6,730,118 B2 | 5/2004 | Spenser et al. |
| 6,733,525 B2 | 5/2004 | Yang et al. |
| 6,741,885 B1 | 5/2004 | Park et al. |
| 6,764,508 B1 | 7/2004 | Roehe et al. |
| 6,764,510 B2 | 7/2004 | Vidlund et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,797,002 B2 | 9/2004 | Spence et al. |
| 6,800,090 B2 | 10/2004 | Alferness et al. |
| 6,802,860 B2 | 10/2004 | Cosgrove et al. |
| 6,805,710 B2 | 10/2004 | Bolling et al. |
| 6,805,711 B2 | 10/2004 | Quijano et al. |
| 6,858,039 B2 | 2/2005 | McCarthy |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,918,917 B1 | 7/2005 | Nguyen et al. |
| 6,921,407 B2 | 7/2005 | Nguyen et al. |
| 6,939,365 B1 | 9/2005 | Fogarty et al. |
| 6,942,694 B2 | 9/2005 | Liddicoat et al. |
| 6,955,689 B2 | 10/2005 | Ryan et al. |
| 6,966,924 B2 | 11/2005 | Holmberg |
| 6,986,775 B2 | 1/2006 | Morales et al. |
| 7,011,681 B2 | 3/2006 | Vesely |
| 7,025,780 B2 | 4/2006 | Gabbay |
| 7,033,322 B2 | 4/2006 | Silver |
| 7,052,466 B2 | 5/2006 | Scheiner et al. |
| 7,070,616 B2 | 7/2006 | Majercak et al. |
| 7,082,330 B2 | 7/2006 | Stadler et al. |
| 7,097,659 B2 | 8/2006 | Woolfson et al. |
| 7,101,395 B2 | 9/2006 | Tremulis et al. |
| 7,101,396 B2 | 9/2006 | Artof et al. |
| 7,118,595 B2 | 10/2006 | Ryan et al. |
| 7,125,421 B2 | 10/2006 | Tremulis et al. |
| 7,147,663 B1 | 12/2006 | Berg et al. |
| 7,153,324 B2 | 12/2006 | Case et al. |
| 7,166,126 B2 | 1/2007 | Spence et al. |
| 7,166,127 B2 | 1/2007 | Spence et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| 7,294,148 B2 | 11/2007 | McCarthy |
| RE40,377 E | 6/2008 | Williamson, IV et al. |
| 7,416,530 B2 | 8/2008 | Turner et al. |
| 7,422,603 B2 | 9/2008 | Lane |
| 7,503,929 B2 | 3/2009 | Johnson et al. |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,691,143 B2 | 4/2010 | Wright et al. |
| 7,916,013 B2 | 3/2011 | Stevenson |
| 7,998,151 B2 | 8/2011 | St. Goar et al. |
| 8,066,650 B2 | 11/2011 | Lee et al. |
| 8,152,844 B2 | 4/2012 | Rao et al. |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,401,659 B2 | 3/2013 | Von Arx et al. |
| 8,460,173 B2 | 6/2013 | Schweich, Jr. et al. |
| 8,529,474 B2 | 9/2013 | Gupta et al. |
| 8,622,936 B2 | 1/2014 | Schenberger et al. |
| 9,101,264 B2 | 8/2015 | Acquista |
| 9,101,281 B2 | 8/2015 | Reinert et al. |
| 9,333,076 B1 | 5/2016 | Edquist et al. |
| 9,693,862 B2 | 7/2017 | Campbell et al. |
| RE46,668 E * | 1/2018 | Stobie .................. A61F 2/2427 |
| D827,134 S | 8/2018 | Matsumura |
| D846,122 S | 4/2019 | Pintor |
| 2001/0010018 A1 | 7/2001 | Cosgrove et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0033009 A1 | 2/2003 | Gabbay |
| 2003/0036795 A1 | 2/2003 | Andersen et al. |
| 2003/0040792 A1 | 2/2003 | Gabbay |
| 2003/0040793 A1 | 2/2003 | Marquez |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |

(56) References Cited

U.S. PATENT DOCUMENTS

| | | |
|---|---|---|
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0249452 A1 | 12/2004 | Adams et al. |
| 2004/0249453 A1 | 12/2004 | Cartledge et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0131533 A1 | 6/2005 | Alfieri et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0182487 A1 | 8/2005 | McCarthy et al. |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0256567 A1 | 11/2005 | Lim et al. |
| 2005/0256568 A1 | 11/2005 | Lim et al. |
| 2005/0261765 A1 | 11/2005 | Liddicoat |
| 2005/0267572 A1 | 12/2005 | Schoon et al. |
| 2005/0278022 A1 | 12/2005 | Lim |
| 2005/0283231 A1 | 12/2005 | Haug et al. |
| 2006/0015178 A1 | 1/2006 | Moaddeb et al. |
| 2006/0015179 A1 | 1/2006 | Bulman-Fleming et al. |
| 2006/0020336 A1 | 1/2006 | Liddicoat |
| 2006/0025857 A1 | 2/2006 | Bergheim et al. |
| 2006/0025858 A1 | 2/2006 | Alameddine |
| 2006/0030885 A1 | 2/2006 | Hyde |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |
| 2006/0241743 A1 | 10/2006 | Bergin et al. |
| 2006/0241745 A1 | 10/2006 | Solem |
| 2006/0259136 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0287719 A1 | 12/2006 | Rowe et al. |
| 2007/0005129 A1 | 1/2007 | Damm et al. |
| 2007/0010876 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100440 A1 | 5/2007 | Figulla et al. |
| 2007/0129794 A1 | 6/2007 | Realyvasquez |
| 2007/0142906 A1 | 6/2007 | Figulla et al. |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0179602 A1 | 8/2007 | Wright |
| 2007/0179604 A1 | 8/2007 | Lane |
| 2007/0185565 A1 | 8/2007 | Schwammenthal et al. |
| 2007/0198097 A1 | 8/2007 | Zegdi |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0233237 A1 | 10/2007 | Krivoruchko |
| 2007/0239266 A1 | 10/2007 | Birdsall |
| 2007/0239269 A1 | 10/2007 | Dolan et al. |
| 2007/0239273 A1 | 10/2007 | Allen |
| 2007/0255398 A1 | 11/2007 | Yang et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0282436 A1 | 12/2007 | Pinchuk |
| 2007/0288089 A1 | 12/2007 | Gurskis et al. |
| 2008/0033543 A1 | 2/2008 | Gurskis et al. |
| 2008/0046040 A1 | 2/2008 | Denker et al. |
| 2008/0119875 A1 | 5/2008 | Ino et al. |
| 2008/0154356 A1 | 6/2008 | Obermiller et al. |
| 2008/0319543 A1 | 12/2008 | Lane |
| 2009/0036903 A1 | 2/2009 | Ino et al. |
| 2009/0076599 A1 | 3/2009 | Bergin |
| 2009/0192591 A1 | 7/2009 | Ryan et al. |
| 2009/0192599 A1 | 7/2009 | Lane et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192606 A1 | 7/2009 | Gloss et al. |
| 2009/0259305 A1 | 10/2009 | Lane et al. |
| 2010/0030329 A1 | 2/2010 | Frater |
| 2010/0049313 A1 | 2/2010 | Alon et al. |
| 2010/0145438 A1 | 6/2010 | Barone |
| 2010/0191326 A1 | 7/2010 | Alkhatib |
| 2010/0256723 A1 | 10/2010 | Murray |
| 2011/0276128 A1 | 11/2011 | Cao et al. |
| 2012/0123284 A1 | 5/2012 | Kheradvar |
| 2012/0136434 A1 | 5/2012 | Carpentier et al. |
| 2012/0158128 A1 | 6/2012 | Gautam et al. |

(56) References Cited

U.S. PATENT DOCUMENTS

| | | | |
|---|---|---|---|
| 2012/0296382 A1 | 11/2012 | Shuros et al. |
| 2013/0144379 A1 | 6/2013 | Najafi et al. |
| 2014/0128964 A1 | 5/2014 | Delaloye |
| 2014/0188221 A1 | 7/2014 | Chung et al. |
| 2014/0364707 A1 | 12/2014 | Kintz et al. |
| 2015/0045635 A1 | 2/2015 | Tankiewicz et al. |
| 2016/0045316 A1 | 2/2016 | Braido et al. |
| 2016/0242903 A1 | 8/2016 | Edquist et al. |
| 2019/0321170 A1 | 10/2019 | Green et al. |
| 2020/0237510 A1 | 7/2020 | Carlino et al. |

FOREIGN PATENT DOCUMENTS

| | | | |
|---|---|---|---|
| EP | 0143246 A2 | 6/1985 |
| EP | 0338994 A1 | 10/1989 |
| EP | 1034753 A1 | 9/2000 |
| SU | 1116573 A1 | 7/1985 |
| SU | 1697790 A1 | 12/1991 |
| WO | 9213502 A1 | 8/1992 |
| WO | 9302640 A1 | 2/1993 |
| WO | 9742871 A1 | 11/1997 |
| WO | 9814138 A1 | 4/1998 |
| WO | 9949816 A1 | 10/1999 |
| WO | 0108608 A1 | 2/2001 |
| WO | 03020178 A1 | 3/2003 |

OTHER PUBLICATIONS

Adams, David, et al., "Large Annuloplasty Rings Facilitate Mitral Valve Repair in Barlow's Disease," Society of Thoracic Surgeons 42.sup.ndAnnual Meeting, Jan. 30-Feb. 1, 2006.
Alonso-Lei, M.D., et al., Adjustable Annuloplasty for Tricuspid Insufficiency, The annals of Thoracic Surgery, vol. 46, No. 3, pp. 368-369, Sep. 1988.
Bolling, et al., Surgical Alternatives for Heart Failure, The Journal of Heart and Lung Transplantation, vol. 20, No. 7, pp. 729-733, 2001.
Bolling, Mitral Valve Reconstruction in the Patient With Heart Failure, Heart Failure Reviews, 6, pp. 177-185, 2001.
Brochure of "Cosgrove-Edwards Annuloplasty System," 2000.
Carpentier, et al. "The 'Physio-Ring': An Advanced Concept in Mitral Valve Annuloplasty," Society of Thoracic Surgeons 31.sup.st Annual meeting, Jan. 30-Feb. 2, 1995.
Carpentier-Edwards Classic Annuloplasty Ring With Duraflo Treatment Models 4425 and 4525 for Mitral and Tricuspid Valvuloplsty, Baxter Healthcare Corporation, 1998.
Flachskampf, Frank A., et al. "Analysis of Shape and Motion of the Mitral Annulus in Subjects With and Without Cardiomyopathy by Echocardiographic 3-Dimensional Reconstruction," American Society of Echocardiography 0894-7317/2000.
Gatti, et al., Preliminary Experience in Mitral Valve Repair Using the Cosgrove-Edwards Annuloplasty Ring, Interactive Cardiovascular and Thoracic Surgery, vol. 2(3), pp. 256-261, 2003.
International Search Report from corresponding PCT Application No. PCT/US2009/043359 dated Aug. 4, 2009.
Melo, et al., Atrioventricular Valve Repair Using Externally Adjustable Flexible Rings: The Journal of Thoracic Cardiovascular Surgery, vol. 110, No. 5, 1995.
MGH Study Shows Mitral Valve Prolapse not a Stroke Risk Factor, Massachusetts General Hospital, pp. 1-3, Jun. 1999.
Salgo, et al., Effect of Annular Shape on Leaflet Curvature in Reducing Mitral Leaflet, American Heart Association, Circulation 200; pp. 106-711.
Seguin, et al., Advance in Mitral Valve Repair Using a Device Flexible in Three Dimensions, The St. Jude Medical-Seguin Annuloplasty Ring, ASAIO Journal, vol. 42, No. 6, pp. 368-371, 1996.
Smolens, et al., Mitral Valve Repair in Heart Failure, The European Journal of Heart Failure 2, pp. 365-371, 2000.
Watanabe, Nozomi, et al. "Mitral Annulus Flattens in Ischemic Mitral Regurgitation: Geometric Differences Between Inferior and Anterior Myocardial Infarction: A Real-Time 3-Dimensional Echocardiographic Study," American Heart Association .COPYRGT. 2005; ISSN: 1524-4539.
Carpentier-Edwards Pyshio Annuloplasty Ring, Edwards Lifesciences Corporation, 2003.
D.C. Miller, IMR Redux—To Repair or Replace?, Journal of Thoracic & Cardiovascular Surgery, pp. 1-8, 2001.

* cited by examiner

VALVE HOLDER ASSEMBLY WITH SUTURE LOOPING PROTECTION

CROSS REFERENCE TO RELATED APPLICATIONS

This application is a continuation of International Patent Application No. PCT/US2020/064895, filed Dec. 14, 2020, which claims the benefit of U.S. Patent Application No. 62/948,744, filed Dec. 16, 2019, the entire disclosures all of which are incorporated by reference for all purposes.

TECHNICAL FIELD

The present disclosure generally concerns medical devices and tools for delivering medical devices. More specifically, the disclosure relates to the surgical replacement of native heart valves that have malformations and/or dysfunctions with prosthetic heart valves that can be implanted through a minimally sized incision. Embodiments of the invention relate to prosthetic heart valves, and to holders for facilitating the implantation of the prosthetic heart valves at native heart valves sites, for example, for a mitral valve replacement procedure.

BACKGROUND

Referring first to FIG. 1, the human heart is generally separated into four pumping chambers which pump blood through the body. Each chamber is provided with its own one-way exit valve. The left atrium receives oxygenated blood from the lungs and advances the oxygenated blood to the left ventricle through the mitral (or bicuspid) valve. The left ventricle collects the oxygenated blood from the left atrium and pushes it through the aortic valve to the aorta, where the oxygenated blood is then distributed to the rest of the body. Deoxygenated blood from the body is then collected at the right atrium and advanced to the right ventricle through the tricuspid valve. The right ventricle then advances the deoxygenated blood through the pulmonary valve and the pulmonary arteries to the lungs to again supply the blood with oxygen.

Each of the valves associated with the chambers of the heart are one-way valves that have leaflets to control the directional flow of the blood through the heart and to prevent backflow of the blood into other chambers or blood vessels that are upstream of the particular chamber. The valves are each supported by an annulus having a dense fibrous ring attached either directly or indirectly to the atrial or ventricular muscle fibers.

When a valve becomes diseased or damaged, the efficiency and/or general functionality of the heart may be compromised. Diseased heart valves may be categorized as either stenotic, wherein the valve does not open sufficiently to allow adequate forward flow of blood through the valve, and/or incompetent, wherein the valve does not close completely, causing excessive backward flow of blood through the valve when the valve is closed. Valve disease can be severely debilitating and even fatal if left untreated.

Various surgical techniques can be performed to replace a diseased or damaged valve. For example, the leaflets of a diseased or damaged native valve may be at least partially removed to prepare the valve annulus for receiving a prosthetic replacement valve. FIG. 2 shows an example of one type of popular prosthetic replacement valve 1 that is a tissue-type bioprosthetic valve generally constructed with three natural-tissue valve leaflets 2, made for example, from porcine tissue or bovine pericardium, or from synthetic or semisynthetic material, that are mounted on a surrounding cloth-covered valve stent structure or frame 3. The shape and structure of the leaflets 2 are supported by a number of commissure posts 4 formed by the frame 3 and positioned circumferentially around the frame 3. In these valves, a biocompatible cloth-covered suture or sewing ring 5 having an inflow side 7 can also be provided on the stent structure 3 of the valve 1, to facilitate easier attachment to the native valve annulus. Such prosthetic valves function much like natural human heart valves, where the leaflets coapt against one another to affect the one-way flow of blood. Examples of such a prosthetic valve are described more fully in U.S. Pat. Nos. 8,986,374 and 7,776,084, both of which are incorporated herein by reference in their entireties for all purposes.

When implanting a tissue type prosthetic valve as described above at a native valve annulus, a number of sutures may be involved in the attachment process, many of which may be pre-installed for providing a track on which the valve is advanced, or "parachuted," until it is properly positioned at the implant site. Additional sutures may also be applied between the prosthetic valve and the heart walls after proper placement, to securely attach or hold the valve implant in place.

Depending on the direction of implantation, for example with some mitral valve replacement procedures, commissure posts of the stent or frame, or other portions of the prosthetic valve, may be pointed distally and advanced on a blind side of the valve, thereby obstructing visibility of the posts or other portions during advancement and implantation. Such procedures can also require a prosthetic valve and its holder to fit through an incision of approximately 15-20 mm in its narrowest direction or dimension. Meanwhile, in some cases, the prosthetic valves are implanted through small access channels using one of various minimally invasive surgical procedures, where visibility at the implant site may be impeded or obstructed.

Each of the above factors may lead to tangling of the sutures with the valve prosthesis, most commonly with the commissure posts of the frame, because the commissure posts provide a protrusion on which the sutures can easily loop around and tangle. This type of entanglement of sutures with prosthetic valves is referred to as "suture looping," which specifically refers to instances where a suture is inadvertently wrapped around one or more of the commissure post tips, where it can then migrate towards and damage the leaflets or interfere with proper leaflet coaptation or other valve operation when the sutures are tightened or secured, resulting in improper valve operation. In some cases, such tangling may not be apparent to the practitioner at the time of implantation, and will only be revealed some time later when valve operation is observed to be improper or other complications arise in the patient, in which case, it may be necessary to initiate another procedure to repair or replace the prosthetic valve.

Attempts have been made to resolve the issue of suture looping, some of which involve holders, which hold the prosthetic valves during delivery of the valves to the native valve annulus. Examples of replacement valve implant procedures are described in more detail in U.S. Patent Application Publication No. 2018/0116795, the contents of which are incorporated herein by reference in their entirety. In one example, a holder has a ratchet or cinching mechanism that bends or folds the commissure posts of the prosthetic valve radially inwardly during delivery, such that the ends of the commissure posts are pointed inwards to reduce the possibility of sutures catching against or looping around the commissure posts. After the valve prosthesis is delivered to the implant site, the holder is removed thereby releasing and expanding the commissure posts to their original positions.

An additional safety feature of the referenced publication is that the prosthetic valve is prevented from being implanted prior to activating the commissure posts, for example, via a removable activator dial, thereby reducing or eliminating mistakes caused by user error. In particular, the dial is not removed until the system is activated, and while in place, the activator dial prevents the valve from being implanted. In some embodiments, the holder includes a removable handle that cannot be connected to the system until the activator dial is removed. The holder also provides for integrated alignment features or other safety features associated with the ratchet mechanism, such that over-deployment or under-deployment of the holder is prevented.

In the above design, the commissure posts are urged radially inward by deployment sutures that connect the valve holder to the valve commissures at several locations. One particular set of locations requires the monofilament suture to be sewn through multiple layers of cloth at each of the commissure tips of the valve. This is ergonomically undesirable for the assemblers as they have to exert a large amount of force with their fingertips to pinch the needles and drive the monofilament suture through the layers of cloth. Suturing through the layers of cloths also leaves a lump of cloth above the monofilament suture, where this lump can potentially snare implantation sutures during valve implantation, leading to suture looping.

In another aspect of the prior design, the suture routing used to pull the commissure tips closer together results in the suture contacting the leaflets near their free edges, thereby creating the possibility of damaging the leaflets. In addition, early bench testing showed that the suture routing was not always effective in preventing suture looping, which is the main function of the holder system. In another design, the routing was slightly modified so that the sutures formed a triangle between the three commissures which was able to deflect possible suture loops during implantation. One drawback of this modified routing, however, was an increase in the force required to remove the holder from the valve due to the additional routing.

In view of the above, it is desirable to have a prosthetic heart valve implant assembly that reduces the possibility of suture looping while improving device usability during implantation. The design disclosed herein ensures a more consistent operation and improves assembly and stability while maintaining and improving safety features of previous designs. In addition, suture routing is improved to prevent contact with valve leaflets and to reduce removal forces.

SUMMARY

In one embodiment of the present invention, a prosthetic heart valve has a plurality of valve leaflets that control directional flow of blood through a heart and a stent structure having a plurality of commissure posts supporting the valve leaflets. The stent structure has a covering over the plurality of commissure posts and has a sewing ring at an inflow end of the stent structure. Each of the plurality of commissure posts has a tip and a suture loop attached to the covering at a location adjacent to or on the tip of the commissure post. Each suture loop provides a passage for a suture to pass through between the covering and the suture loop. The suture loop may be aligned with the tip of the commissure post or may be aligned perpendicular to the tip of the commissure post.

In another embodiment, each commissure post has an additional suture loop or loops attached to the covering at a location adjacent to or on the tip of the commissure post. The first suture loop and the additional suture loop or loops are aligned to provide a single passage for a suture to pass through between the covering and the suture loops. Alternatively, the additional suture loop may lay across the first suture loop or may be located end to end to provide two adjacent passages for a suture or sutures to pass through between the covering and the suture loops.

In another embodiment, a valve holder assembly includes a prosthetic heart valve as described above and a valve holder. In addition, a first deployment suture connects the valve holder to the prosthetic heart valve. The first deployment suture is attached to the valve holder, routed through the suture loop, and back to the valve holder.

In one embodiment, there are two commissure posts and the first deployment suture is attached to the valve holder, routed through the suture loop of a first commissure post, routed through the suture loop of a second commissure post, and back to the valve holder. Furthermore, the first deployment suture may be attached to the valve holder, routed through the sewing ring, through the suture loop of the first commissure post, through the suture loop of the second commissure post, again through the sewing ring, and back to the valve holder.

In another embodiment, the valve holder further includes a second deployment suture connecting the valve holder to the prosthetic heart valve. The second deployment suture is attached to the valve holder, routed through the suture loop of the second commissure post, and back to the valve holder. Further, the embodiment may include a second suture loop of the second commissure post. The first suture loop and the second suture loop are located end to end to provide two adjacent passages for a suture or sutures to pass through between the covering and the suture loops.

In another embodiment, a valve holder assembly includes a valve holder body to hold a prosthetic heart valve. The valve holder body has a top surface, a bottom surface, and a central axis. A rotor is insertable through the top surface and positioned in the valve holder body. When a prosthetic heart valve is coupled to the valve holder body, the rotor is rotatable around the central axis of the valve holder body to adjust the prosthetic heart valve to a delivery position. A guide body is mounted to the valve holder body and projects above the upper surface of the valve holder body. The guide body has an opening through which an activator is couplable to the rotor for rotating the rotor around the central axis of the valve holder body. A handle adapter is insertable into the opening of the guide body along the central axis. The handle adapter has an opening through which the activator is couplable to the rotor for rotating the rotor around the central axis of the valve holder body. The opening of the handle is also configured to receive a handle.

In a further embodiment, the valve holder body has a snap arm that flexes to engage a stop of the guide body to secure the valve holder body and the guide body together. The valve holder assembly may further include an attachment suture. The guide body has an arm extending from the front of the guide body and the arm has a recess along a bottom of the arm. The guide body may also have a stop extending from the back of the guide body and the stop has a recess along a bottom of the stop. The handle adapter may have a suture mount extending from the front of the handle adapter and the suture mount may have a recess along a top of the suture mount. In addition, the handle adapter may have a suture support extending from the back of the handle adapter and the suture support may have a recess along a top of the suture support. The attachment suture may then be secured in the recesses of the arm and the stop of the guide body and in the recesses of the suture support and the suture mount of the handle adapter.

In another embodiment, the handle adapter has a ledge and a gap is formed between the ledge of the handle adapter and a top surface of the guide body. The attachment suture may be located in the gap to hide the suture routing from view.

The valve holder body may also have a central opening and the rotor extends through the central opening below a bottom of the valve holder body.

In another embodiment, the guide body has a cutting well comprising two arms extending from the guide body, a top of each arm has a suture recess and the arms are spaced apart to form an opening to permit cutting of a suture across the arms of the cutting well.

In another embodiment, the valve holder assembly has an activator dial connectable to the rotor for rotating the rotor around the central axis of the body. The activator dial has a flange and the handle adapter has a corresponding rib. The activator dial is rotatable in one direction and stops at a location where the flange engages the rib.

BRIEF DESCRIPTION OF THE DRAWINGS

Further features and advantages of the invention will become apparent from the description of embodiments using the accompanying drawings. In the drawings.

DETAILED DESCRIPTION

The valve holders disclosed herein are particularly useful for avoiding suture looping and other valve damage during advancement of the prosthetic valves to the implant sites, as well as preventing damage during final suturing of the valves at the native valve annulus. In mitral valve replacement procedures, commissure posts of the prosthetic valve point distally away from practitioners, and in the direction of valve advancement, and may be more prone to suture looping or other entangling. For such procedures, valve holders can be deployed to bend or fold the commissure posts radially inward toward a center of the valve to reduce or eliminate suture looping. Such procedures can also include features that prevent valve implantation until the commissure posts are in the activated or deployed positions. The holders can also include alignment features that prevent over-deployment or under-deployment. In this fashion, the holders provide ease of use while minimizing or reducing user errors.

The valve holders described herein include various parts that are designed to ensure a more consistent operation of the deployment mechanism to bend the valve commissure posts prior to valve implantation, to implement hard stops to prevent over-deployment and/or to improve assembly and stability between the parts. With regard to the prosthetic heart valve, routing of the sutures to deploy the commissure posts is improved to reduce contact between the routing sutures and the valve leaflets and to reduce the force required to remove the valve holder from the prosthetic valve after implantation.

In another embodiment, retaining loops are attached to the covering of the commissure posts to more precisely define a location where the suture is routed through the valve. Routing the suture underneath the commissure post loops is easier than trying to do the same through multiple layers of cloth. This is more ergonomic for assemblers that have to repeat this task many times during the work day. Also, the combination of the commissure post loop and the suture presents a low profile. This allows the implantation sutures to glide over the commissure post tips more easily, without suture looping.

Figure 1:
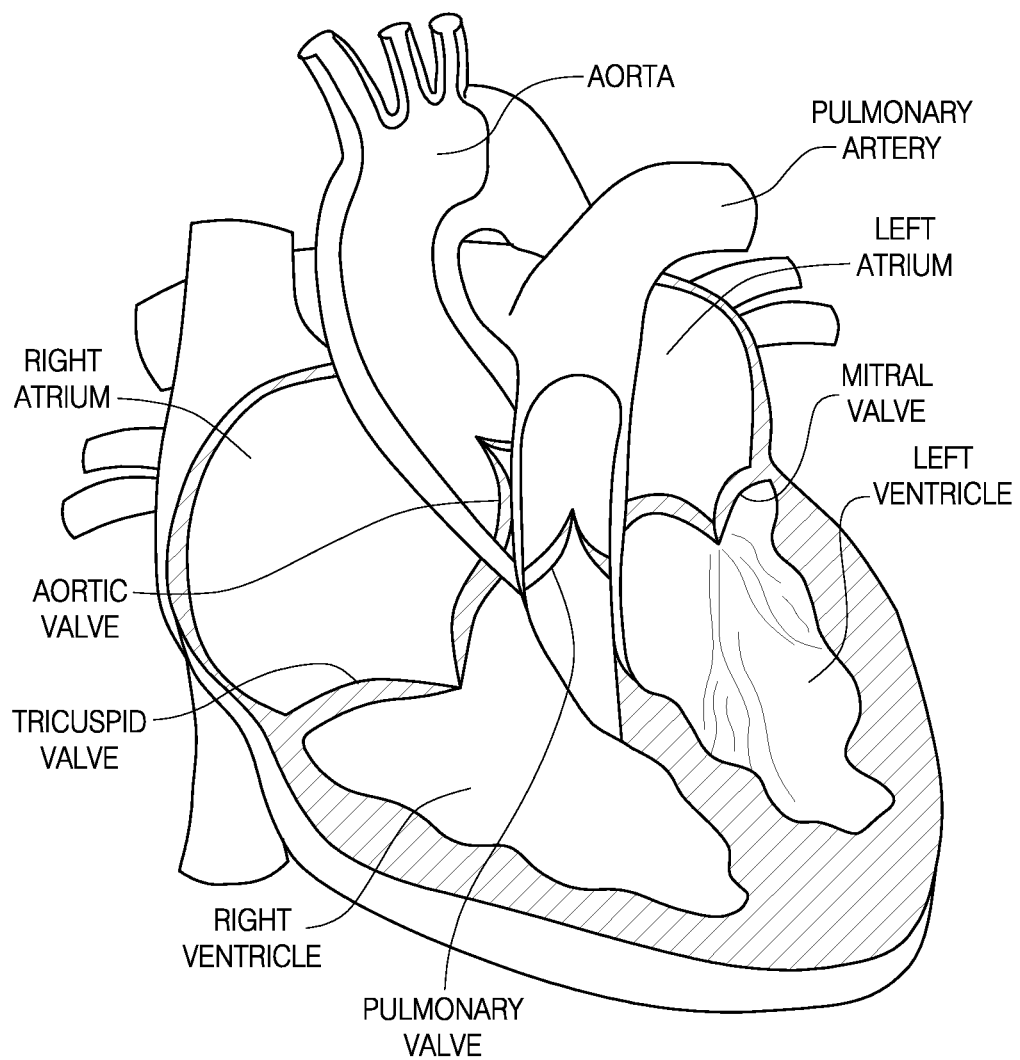
FIG. 1 shows a schematic cross-sectional view of a human heart.
Figure 2:
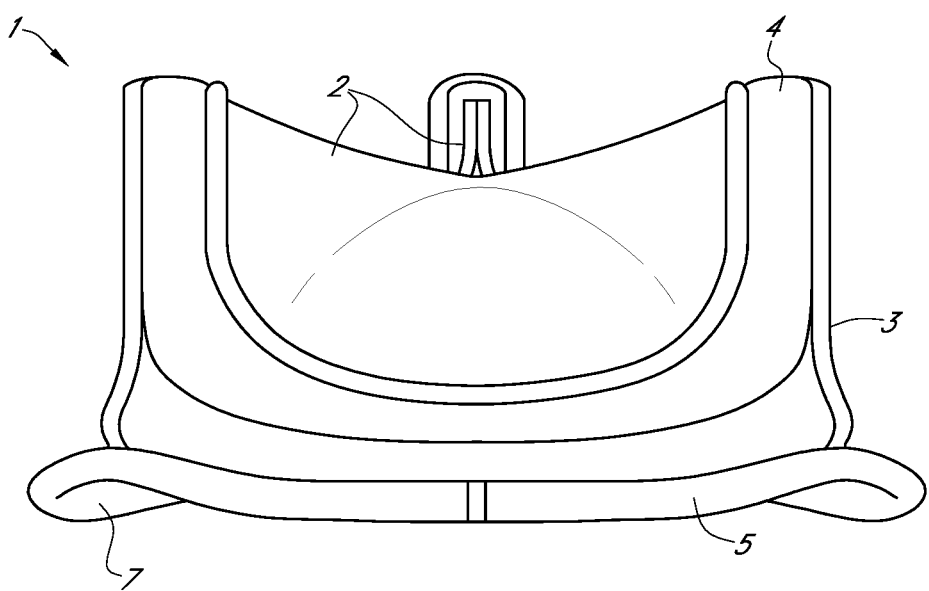
FIG. 2 shows a schematic perspective view of an example of a prosthetic heart valve that can be used with embodiments of the invention.
Figure 3:
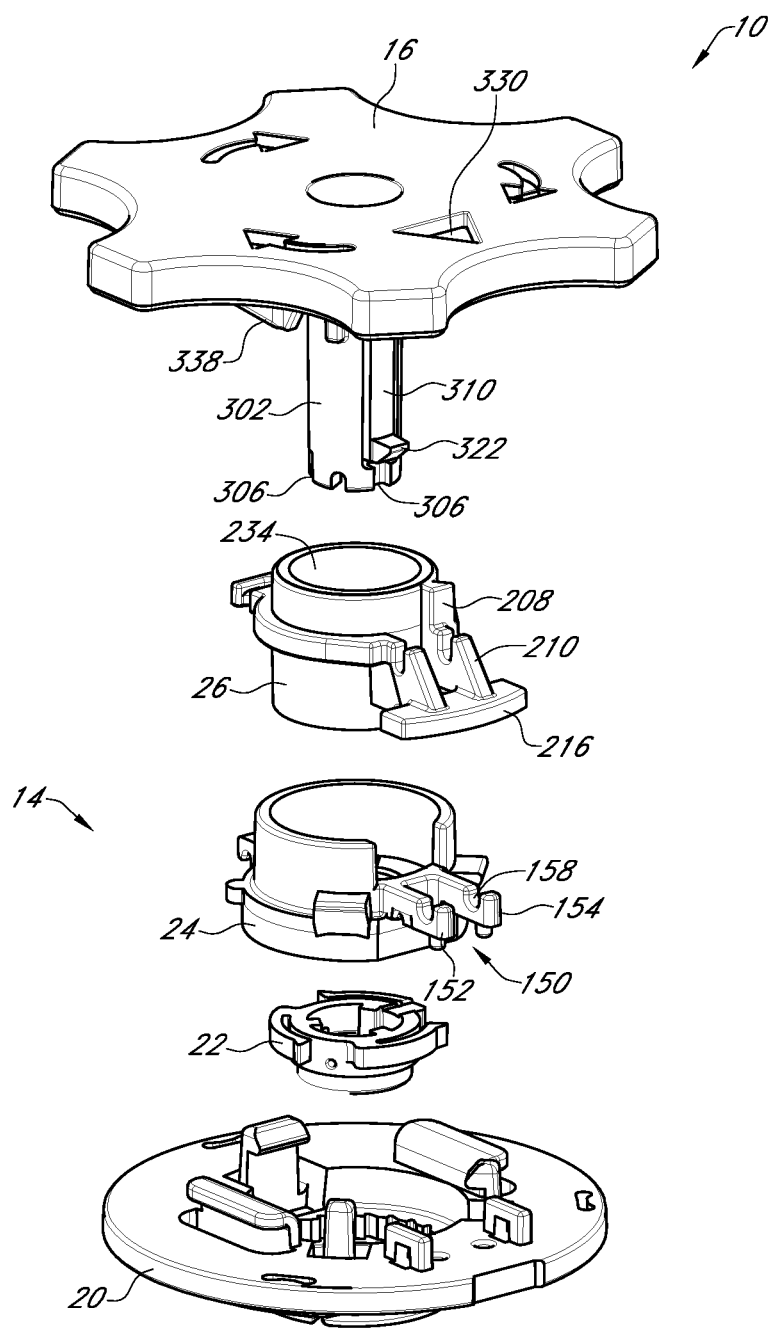
FIG. 3 shows an exploded perspective view of a heart valve implant holder assembly according to an embodiment of the invention.
Figure 4:
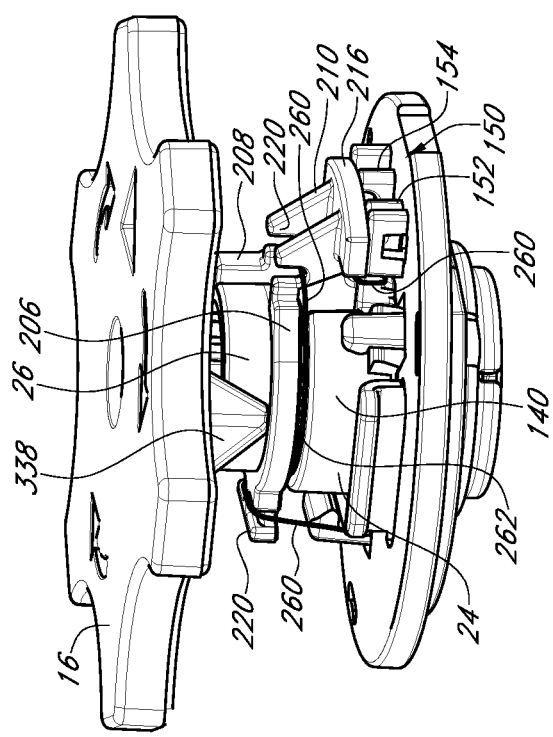
FIG. 4 shows a perspective view of the heart valve implant holder assembly of FIG. 3.

With reference to FIGS. 3-4, a heart valve implant holder assembly 10 includes a valve holder 14 and an activator dial (or actuator) 16. The valve holder 14 includes a valve holder body 20, a rotor 22, a guide body 24 and a handle adapter 26. As described further below, the sewing ring 5 of a prosthetic heart valve (FIG. 2) is attached to the bottom of the valve holder body 20. The rotor 22 is positioned in a bore of the body 20. After attaching the guide body 24 to the valve holder body 20 and attaching the handle adapter 26 to the guide body 24, the implant holder assembly 10 is ready to be activated. The rotor 22 is activated using the activator dial 16 to deploy the valve holder 14 and bend the commissure posts 4 of the prosthetic heart valve to a delivery position or configuration. When deployed, the occurrence of suture looping over the commissure posts 4 of the prosthetic heart valve during the surgical procedure is reduced or eliminated.

Figure 5A:
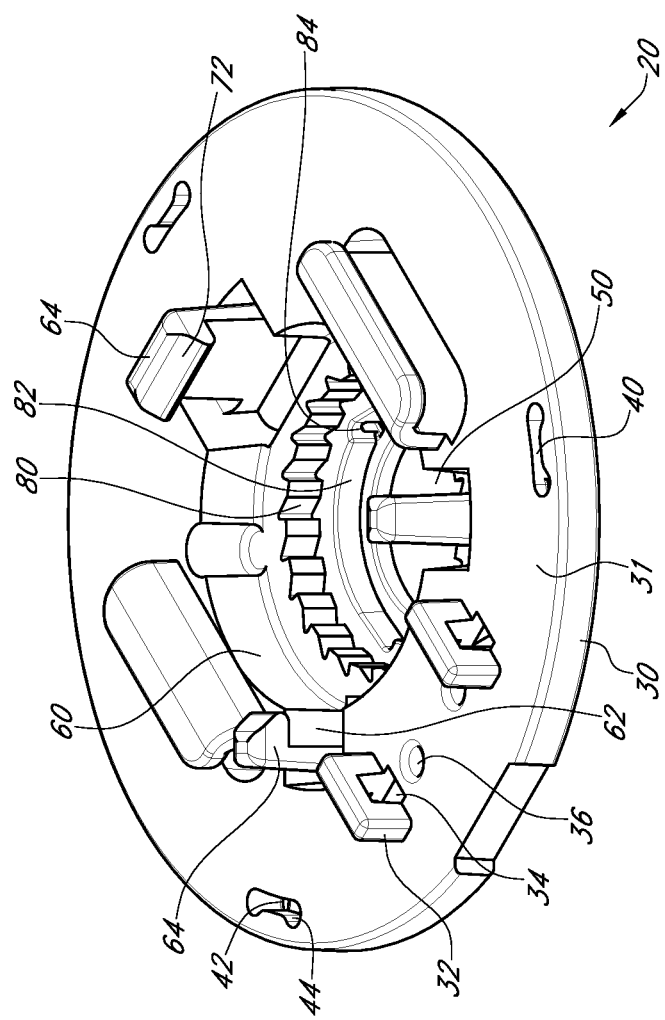
FIG. 5A shows a top perspective view of a valve holder body of the heart valve implant holder assembly of FIG. 3.
Figure 5B:
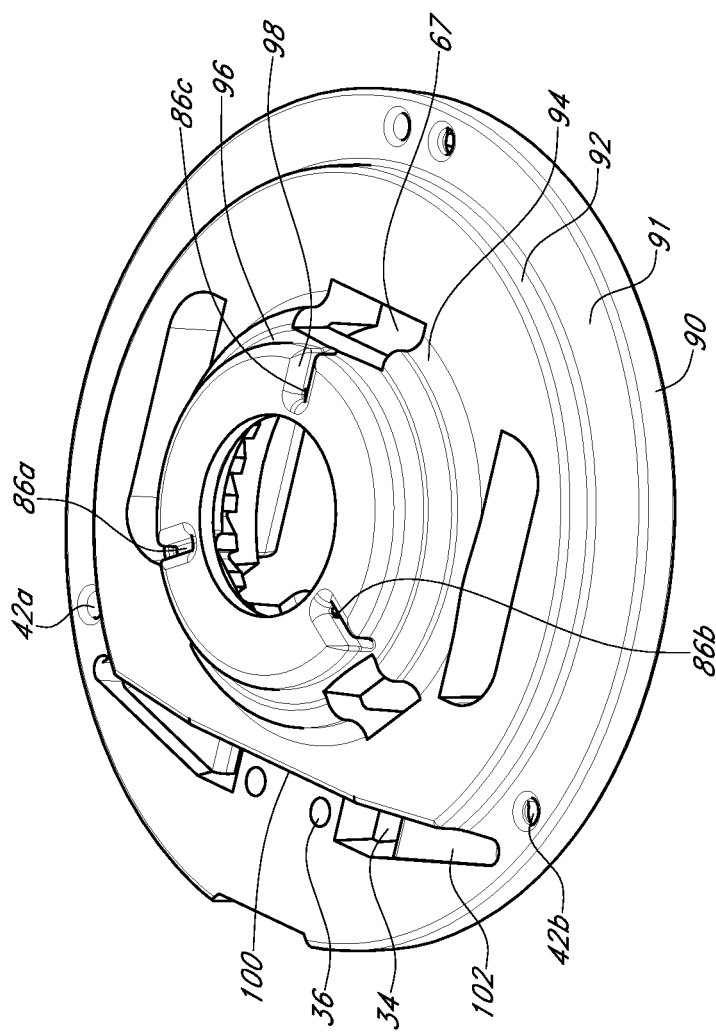
FIG. 5B shows a bottom perspective view of the valve holder body of the heart valve implant holder assembly of FIG. 3.
Figure 5C:
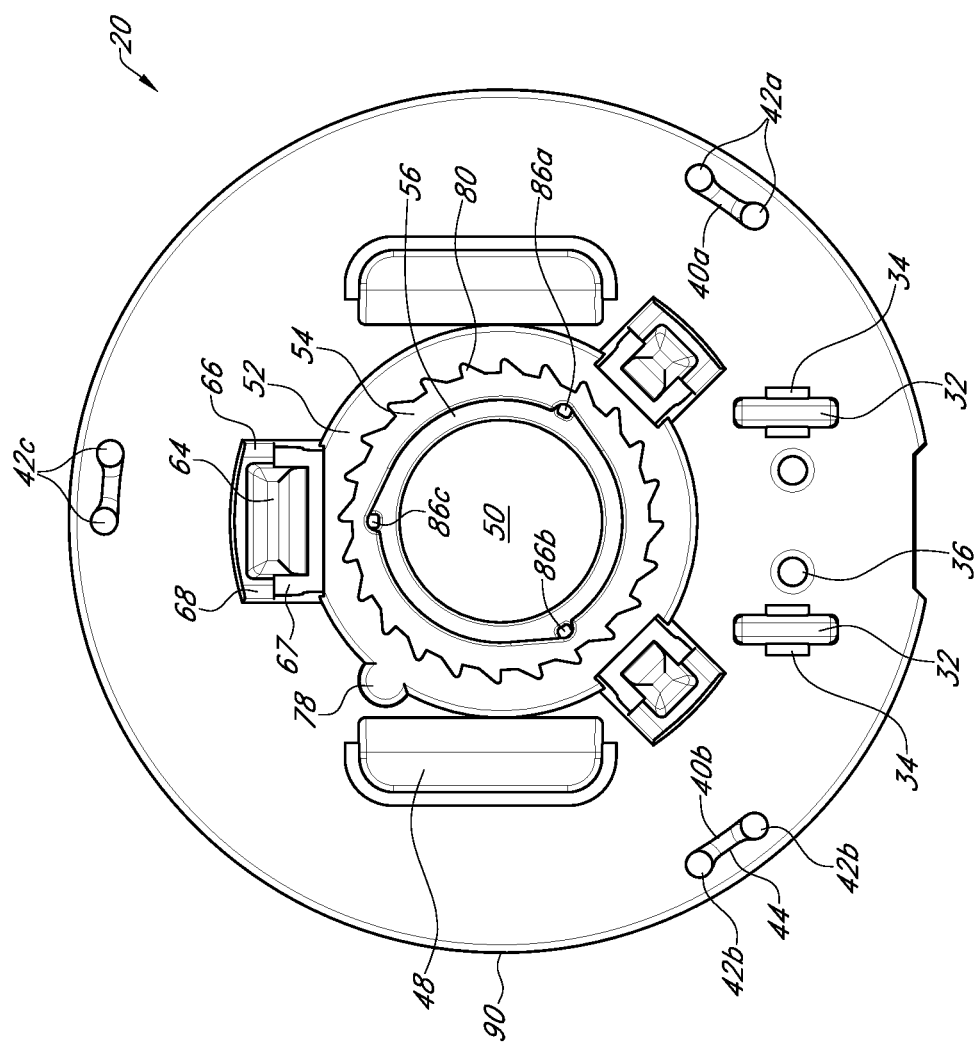
FIG. 5C shows a top view of the valve holder body of the heart valve implant holder assembly of FIG. 3.

With reference to FIGS. 5A-5C, the valve holder body 20 has a circular platform 30 with a flat upper surface 31 and a pair of suture mounts 32 located at a periphery of the platform 30. Each suture mount 32 forms a tunnel above the upper surface 31 of the circular platform. A hole 34 at the base of each tunnel passes through the circular platform. Between the suture mounts 32 are two additional holes 36 located between the holes 32 for receiving pins of the guide body 24. In addition, the valve holder body 20 has three suture openings in the platform 30. Each suture opening includes a recessed area 40 into the upper surface 31 of the platform and a pair of holes 42 at the bottom of the recessed area that pass through the circular platform. Between the holes 42 is a tie strut 44. Each of the holes 34, 42 may be used for routing sutures that are used to deploy the prosthetic heart valve to a deployed position where the commissure posts are angled radially inwards toward the center of the valve to reduce or eliminate suture looping. One way of suturing the prosthetic heart valve to the valve holder to enable this feature is described in detail in U.S. Patent Application Publication No. 2018/0116795. Projecting up from the top of the circular platform 30 are rails 48 for securing the valve holder body 20 to corresponding retainers of a package (not shown) for delivery.

In the valve holder body 20, a central opening 50 is provided for receiving the rotor 22. The opening 50 is stepped to provide three abutment surfaces, namely an upper abutment surface 52, a middle abutment surface 54, and a lower abutment surface 56. At the lower abutment surface 56, the diameter of the opening 50 is smallest.

The upper abutment surface 52 is surrounded by a cylindrical wall 60. At three equidistant locations around the upper abutment surface 52, the cylindrical wall 60 has cutouts 62 forming snap arms 64. In particular, each cutout has a base 66 spaced from the upper abutment surface 52 by an opening 67 through the valve holder body 20. An upper surface 68 of the base 66 is above and parallel to the upper abutment surface. Extending upward from the upper surface 68 is the snap arm 64. A free end of the snap arm has a protrusion that extends towards the center of the valve holder body opening 50. The protrusion includes a ramped surface 72 that increasingly protrudes into the opening 50 from top to bottom. There is space between the snap arm 64 and the back of the cutout 62 to permit the snap arm to flex during assembly of the guide body 24 to the valve holder body 20.

In the present embodiment, two of the snap arms 64, i.e., the arms adjacent the suture mounts 32, have a smaller width than the third snap arm, which is located diametrically opposite the suture mounts. Each of the snap arms has the same height. The widths and heights of the snap arms, however, may all be the same or varied as desired. A tab recess 78 in the cylindrical wall 60 may also be included to align the guide body 24 and the valve holder body 20.

The middle abutment surface 54 is surrounded by a ratchet wall 80 to interact with the rotor 22, as will be described further below. The lower abutment surface 56 is surrounded by a cylindrical wall 82 that is interrupted by three setbacks 84 that are equally spaced apart around the wall. The setbacks 84 provides spaces for passing sutures through the valve holder body 20 through openings 86.

With reference to FIG. 5B, the bottom side of the valve holder body is tiered. The peripheral outer portion of the valve holder body is a rim 90. Extending below the rim are three reduced diameter portions. An upper reduced diameter portion 92 has a smaller diameter than the rim 90 to provide clearance for a connected prosthetic heart valve. A middle reduced diameter portion 94 has a smaller diameter than the upper reduced diameter portion 92. The openings 67 associated with the snap arms are formed through the upper and middle reduced diameter portions 92, 94. A lower reduced diameter portion 96 has the smallest diameter of the reduced diameter portions and forms the openings 86 of the setbacks 84 and additional passages 98 from the openings 86 for the routing of sutures through the valve holder body 20 to the prosthetic heart valve from the rotor 22.

In a preferred embodiment, the upper reduced diameter portion 92 has a setback 100 under the rim 90 to accommodate the passage of sutures through holes 34 and holes 42. In particular, the setback 100 includes two recessed portions 102, each one located to receive one of holes 34 and one of holes 42.

Figure 6:
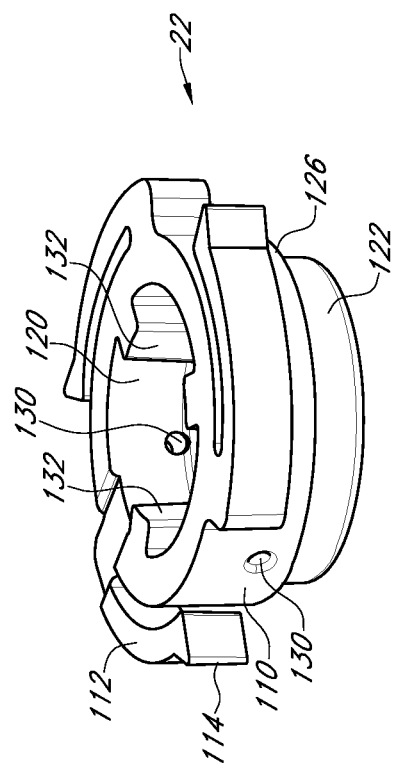
FIG. 6 shows a top perspective view of a valve holder rotor of the heart valve implant holder assembly of FIG. 3.

With reference to FIG. 6, the rotor 22 is configured to be positioned inside of the central opening 50 of the valve holder body 20 and is rotatable with respect to the holder body 20. As will be described later, sutures are connected to the rotor 22 for adjusting the prosthetic heart valve to the delivery position using the activator dial 16. The rotor 22 includes a central portion no and a plurality of outwardly extending flexible arms 112. The flexible arms 112 are resilient such that the arms can be deflected inwards towards the central portion no and then released, causing the arms 112 to spring back into a relaxed shape when no longer deflected.

Figure 10:
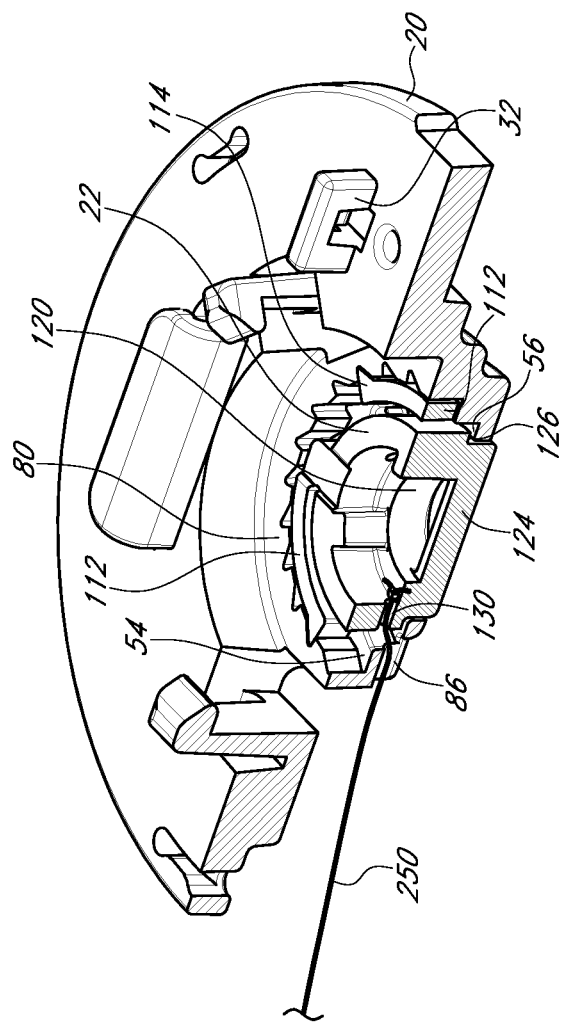
FIG. 10 shows a cross-sectional view of the assembled valve holder body and valve holder rotor of FIG. 4.

End portions of the arms 112 have engagement portions 114 in the form of teeth or pawls to engage the corresponding ratchet wall 80 of the valve holder body 20 in the form of a plurality of notches or grooves (FIG. 10). The teeth 114 of the rotor 22 engage the ratchet wall 80 of the body 20 to provide a one-way ratcheting mechanism that allows the rotor 22 to rotate in one direction relative to the body 20 (e.g., clockwise), but that prevents the rotor 22 from moving in a counter or opposite direction (e.g., counter-clockwise).

The central portion no of the rotor 22 defines a central opening 120 to receive the activator dial 16. Extending below and inset from the central portion no is a lower portion 122 of the rotor 22. The central opening 120 extends through the lower portion. A rib 124 of the lower portion (FIG. 10) intersects the central opening 120. Notably, in a preferred embodiment, the lower portion 122 of the rotor 22 protrudes below the bottom of the valve holder body 20 when assembled. In addition, the bottoms of the flexible arms 112 of the rotor may slide along the middle abutment surface 54 of the valve holder body 20 and/or a stop surface 126 of the central portion no of the rotor may slide along the lower abutment surface 56 of the valve holder body 20 during activation.

The rotor 22 additionally includes one or more holes 130 projecting through a sidewall of the central portion no of the rotor 22 and into the central opening 120. The holes 130 provide attachment points for connecting end regions of the sutures to the rotor 22. When the sutures are connected to the rotor 22, rotation of the rotor 22 will create tension in the suture lines and further cause the sutures to be pulled in the direction of the moving rotor 22. Because the sutures are connected to the commissure posts of the prosthetic valve, this pulling force activates or deploys the valve holder 14 to adjust the prosthetic valve to a collapsed or delivery position by transferring the force onto the commissure posts of the prosthetic valve. The commissure posts are thereby radially bent inwards toward a center of the prosthetic valve.

In order to actuate the rotor 22, the central opening 120 has alignment keys 132 in the shape of longitudinally extending protrusions to mate with alignment keyways 306 of the activator dial 16. With reference to FIG. 3, the activator dial 16 is used by an operator or user to rotate the rotor 22 and adjust the valve holder 14 to the deployed configuration. The activator dial 16 can be assembled with the valve holder 14 prior to use in a surgical procedure. In one embodiment, for example, the activator dial 16 can be preassembled with the valve holder 14 during an assembly process by the manufacturer of the valve holder 14. Such an assembly step prior to use in surgical procedures can be done in order to aid in proper usage of the valve holder 14 and reduce the risk of inadvertent user error.

Figure 9A:
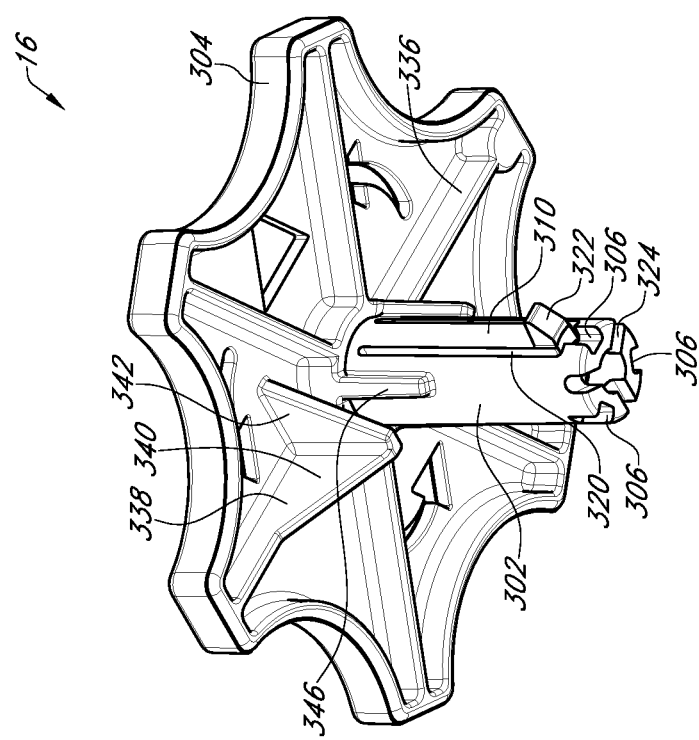
FIG. 9A shows a bottom perspective view of an activator dial of the heart valve implant holder assembly of FIG. 3.
Figure 9B:
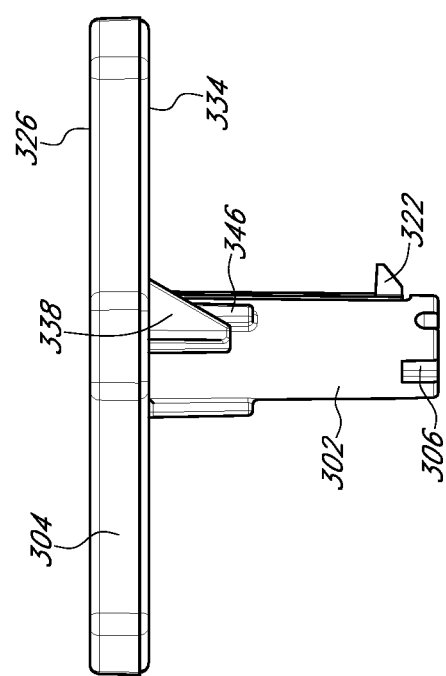
FIG. 9B shows a side view of the activator dial of the heart valve implant holder assembly of FIG. 3.
Figure 9C:
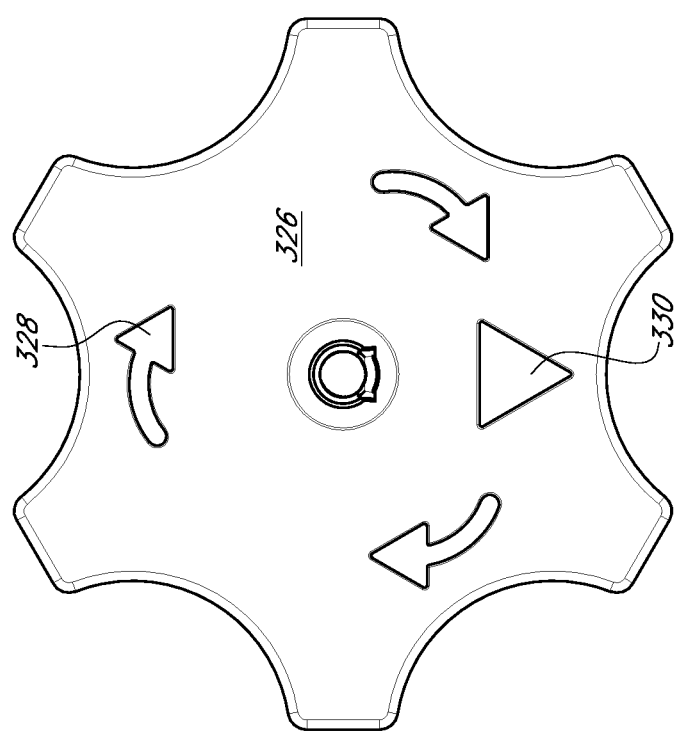
FIG. 9C shows a top view of the activator dial of the heart valve implant holder assembly of FIG. 3.

With reference to FIGS. 9A-9C, the dial 16 includes a central shaft 302 having a central axis, and an enlarged gripping portion 304 extending therefrom. The central shaft 302 is sized and configured to be received in the central opening 120 of the rotor 22. The central shaft 302 includes alignment keyways 306 in the shape of longitudinally extending slots or recesses for coupling to the alignment keys 132 of the rotor 22. The mating of the alignment features 132, 306 enables the rotor 22 to rotate together with the dial 16. In various embodiments, the dial 16 can be turned either manually (for example, by the hands of an operator) or automatically via a motor or other means. Meanwhile, while three mating alignment features 132, 306 are respectively shown, the number of mating alignment features can be different in various embodiments. In one embodiment, for example, a single mating alignment feature can be used.

After the activator dial 16 is used to deploy the commissure posts to a collapsed position, the activator dial 16 may be removed and a handle (not shown) may be attached to the valve holder to deliver the prosthetic heart valve to the native valve site. To securely connect the handle to the valve holder body 20, the guide body 24 and the handle adapter 26 are provided.

Figure 7A:
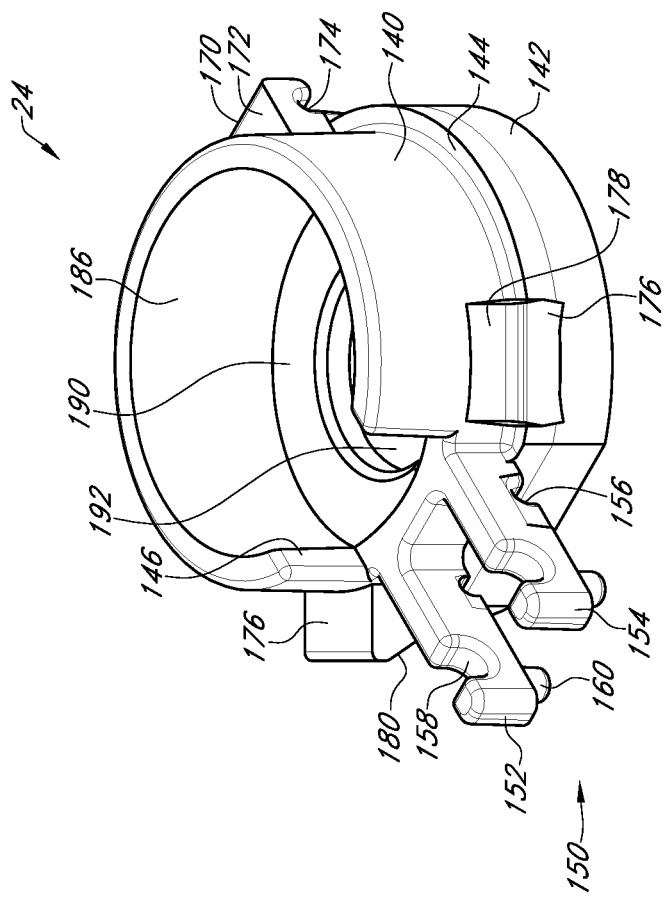
FIG. 7A shows a top perspective view of a guide body of the heart valve implant holder assembly of FIG. 3.
Figure 7B:
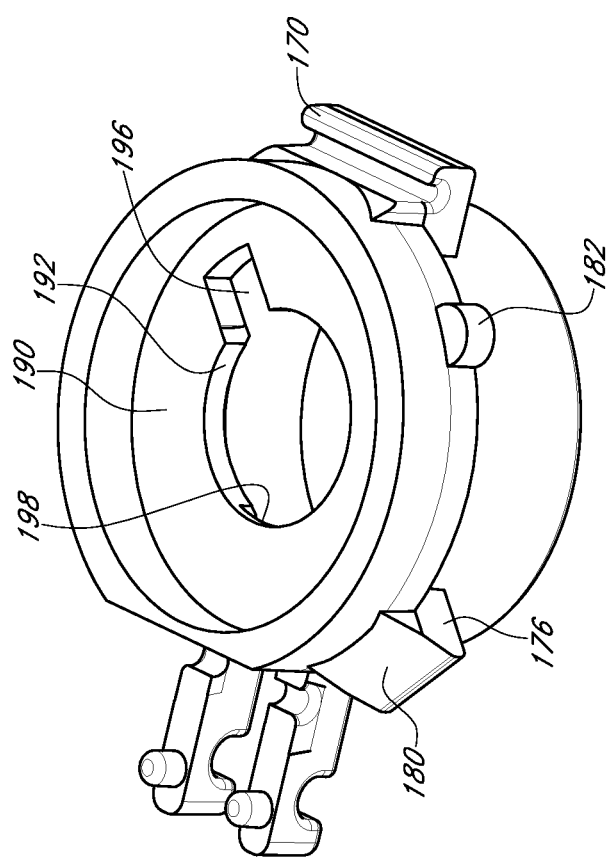
FIG. 7B shows a bottom perspective view of the guide body of the heart valve implant holder assembly of FIG. 3.

With reference to FIGS. 7A and 7B, the guide body 24 has an upper tubular wall 140 and a lower tubular wall 142. The lower wall 142 has a greater outer diameter than the upper wall 140 and fits within the upper portion of the central opening 50 of the valve holder body 20. A ledge 144 separates the upper and lower walls.

The upper tubular wall 140 of the guide body 24 has a cutout 146 on one side. Projecting out from the upper wall 140 just below the cutout 146 is a suture cutting well 150, including a first arm 152 and a second arm 154. The top of each arm has a suture recess 158 and the arms are spaced apart to form the well 150 to permit easy cutting of sutures across the well 150. As will be discussed later, this well receives the sutures that connect the valve holder 14 to the prosthetic heart valve. A post 160 extends downward from the free end of each arm 152, 154. The posts 160 engage the holes 36 of the valve holder body 20 to prevent rotation between the guide body 24 and the valve holder body 20.

The lower tubular wall 142 of the guide body 24 is recessed below the suture cutting well 150. In this area, the arms 152, 154 of the cutting well 150 have recesses 156. As will be discussed later, these recesses 156 receive a suture or sutures for holding the guide body 24 and the handle adapter 26 together.

Spaced equidistantly around the ledge 144 are three stops that project out from the upper and lower walls 140, 142. A first stop 170 is located opposite the cutting well iso. The first stop 170 has a flat upper surface 172 and a recess 174 extending along the bottom of the first stop to receive a suture. The two additional stops 176 are located on either side and adjacent the cutting well iso. Each stop 176 has a flat upper surface 178 and a ramped surface 180 extending from the outer edge of the stop to the lower cylindrical wall of the guide body 142. Notably, the three stops are configured to engage the corresponding snap arms 64 of the valve holder body 20 to secure the guide body 24 and the valve holder body 20 together. (See FIG. 11). Located between one of the stops 176 and the first stop 170 is a tab 182 projecting outwardly from the top of the lower cylindrical wall 142. The tab 182 is oriented to fit in the tab recess 78 of the valve holder body 20 for proper alignment.

An opening 186 extends through the guide body 24. Midway through the guide body 24, a platform 190 extends into the opening 186. The platform 190 defines a central bore 192 having an alignment keyway 196. The upper side of the platform 190 also has a ramp 198. Preferably, the ramp 198 is located adjacent the cutting well 150 of the guide body and is spaced apart from the alignment keyway 196. The ramp 198 and the alignment keyway 196 are configured to permit a flexible arm 310 on the activator dial 16 to pass through and back out of the central bore 192 of the guide body 24 for connecting and disconnecting the activator dial 16 to and from the rotor 22.

Figure 8A:
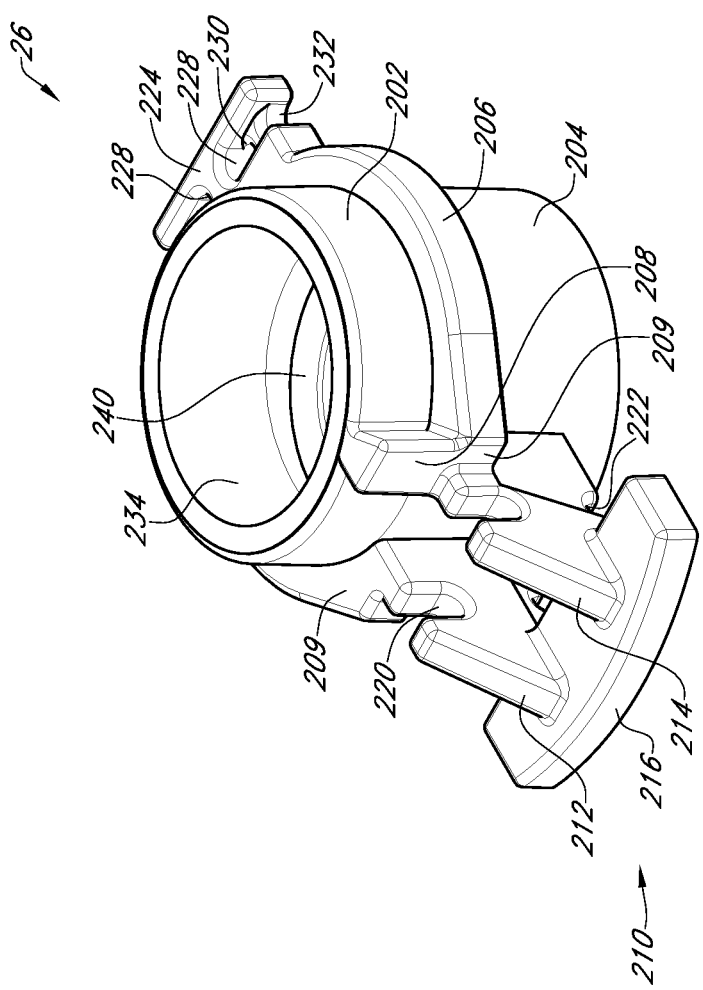
FIG. 8A shows a top perspective view of a handle adapter of the heart valve implant holder assembly of FIG. 3.
Figure 8B:
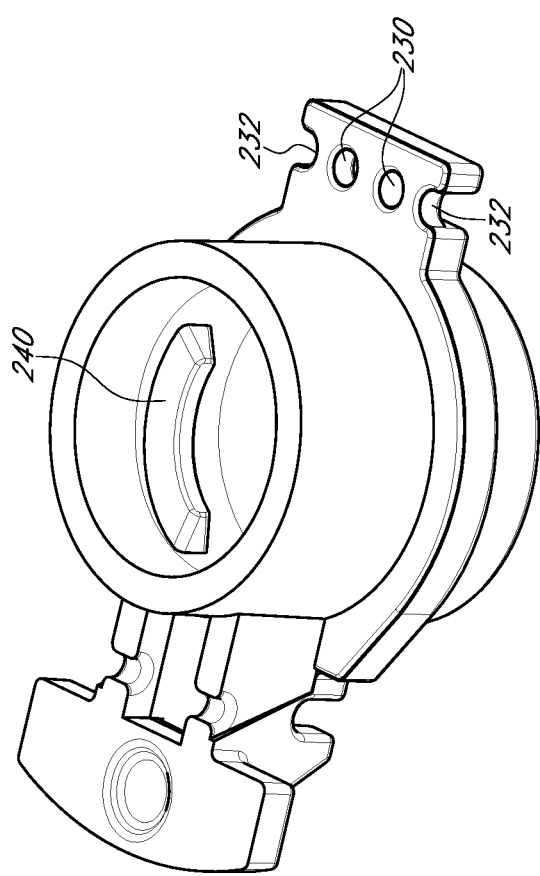
FIG. 8B shows a bottom perspective view of the handle adapter of the heart valve implant holder assembly of FIG. 3.

With reference to FIGS. 8A and 8B, the handle adapter 26 is a cylindrical tube having an upper tubular part 202 and a lower tubular part 204. The lower tubular part 204 is sized to fit inside the opening 186 of the guide body 24. A ledge 206 is arranged around the cylindrical tube between the upper part 202 and the lower part 204.

Projecting up from the top of the ledge is a vertical rib 208 that will interact with a flange 338 on the activator dial 16 to prevent further rotation of the dial 16. At the location of the vertical rib 208, the ledge has extension portions 209 that project further away from the cylindrical tube. A suture mount 210 having a first support 212 and a second support 214 extends from the extension portions 209 and from the lower tubular part 204. Along the top of each support 212 and 214 adjacent the ledge 206 is a recess 220 for a suture. The first and second supports are spaced apart from each other and the space is wide enough to receive a cutting instrument to cut a suture laid across the recesses 220 of the suture mount 210. A shield 216 is mounted at the lower free ends of the supports 212, 214 and projects outwardly and laterally. Also, along the bottom of each support adjacent the ledge is a recess 222 for a suture.

On the opposite side of the adapter 26 from the suture mount 210 is a suture support 224 that projects out from the ledge 206. The suture support 224 has a pair of back-to-back recesses 228. The recesses 228 have through holes 230 located adjacent each other at one end of the recesses and cutouts 232 at the opposite end of the recesses. The holes 230 and cutouts 232 are for securing sutures. Inside the central bore 234 of the cylindrical tube is a screw thread 240. Preferably, the screw thread is an ACME thread and has less than one full turn to facilitate injection molding. The thread also has a first alignment keyway 242 and a second alignment keyway 244 to facilitate insertion and removal of the activator dial 16.

With reference to FIGS. 9A-9C, the activator dial 16 has a tubular central shaft 302 with a flexible arm 310. The flexible arm 310 is spaced apart from the remainder of the central shaft 302 by gaps 320 on either side and at the bottom of the flexible arm 310 such that the flexible arm 310 is movable (e.g., bendable) relative to the remainder of the central shaft 302. The flexible arm 320 may be bent inwards relative to the remainder of the central shaft 302 and towards a central cavity of the dial 16. The flexible arm 320 is resilient such that the flexible arm 310 may be bent by the application of a force and will return to its original shape when the force is removed.

A key 322 at the free end of the flexible arm is configured to engage the ramp 198 of the guide body 24 and has a width suitable to pass through the alignment keyway 196 of the guide body 24. Directly below the flexible arm 320 is one of the keyways 306 for coupling to the rotor 22 as mentioned previously. At the bottom of the central shaft of the dial, additional recesses 324 are provided to assist with suture routing through the rotor.

The gripping portion 304 of the activator dial 16 is scalloped around the periphery to better permit grasping and rotation. An upper surface 326 of the gripping portion is provided with indicia, such as arrows 328 to indicate direction of rotation, and a triangular marker 330 may be used to identify the location of the flexible arm 310 which is obscured from view by the gripping portion during assembly to the valve holder 14.

A bottom surface 334 of the gripping portion has radial struts 336 to improve strength. An angled flange 338 extends down from the bottom surface 334. The flange includes a triangular plate 340 formed as an extension from one of the radial struts 336. A brace plate 342 extends from the triangular plate at 90° to provide strength. Extending down from the bottom of the gripping portion 304 and along the central shaft 302 are a plurality of spacers 346 to assist with aligning the central shaft 302 by engaging the central bore 234 of the handle adapter during assembly.

Figure 14A:
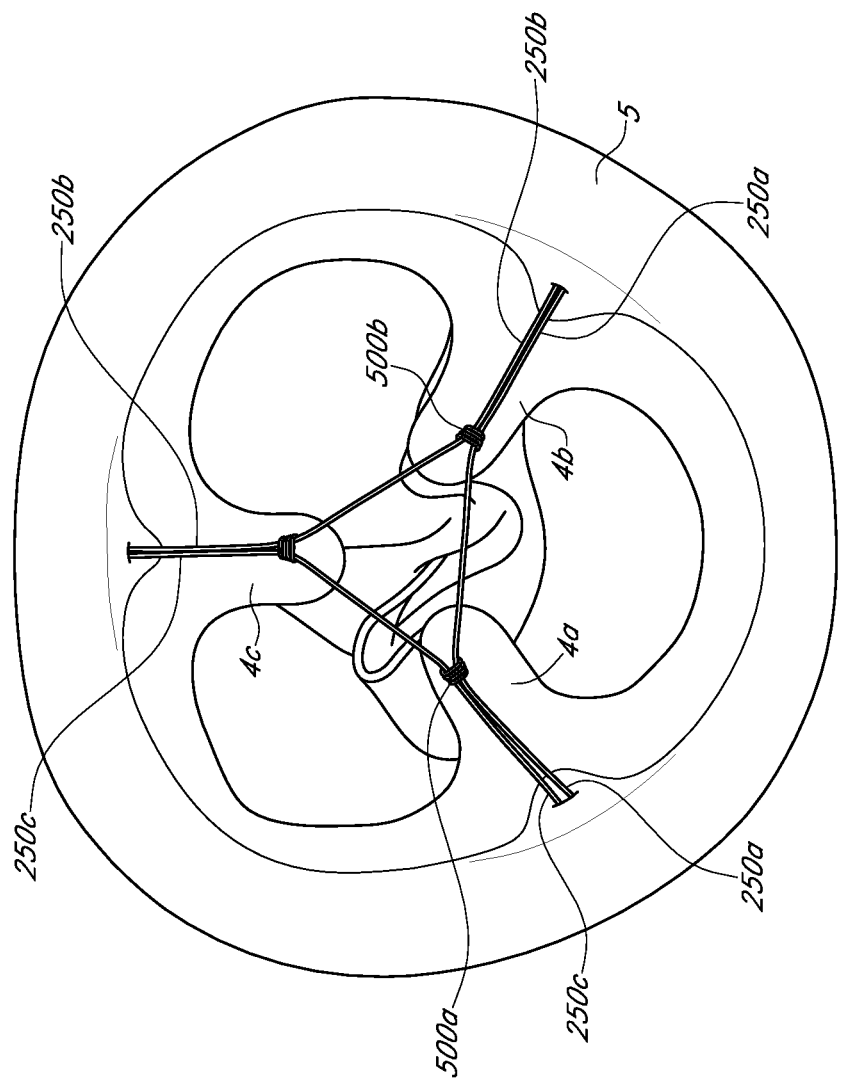
FIG. 14A shows a schematic view of a prosthetic heart valve at the outflow side with suture routing.
Figure 14B:
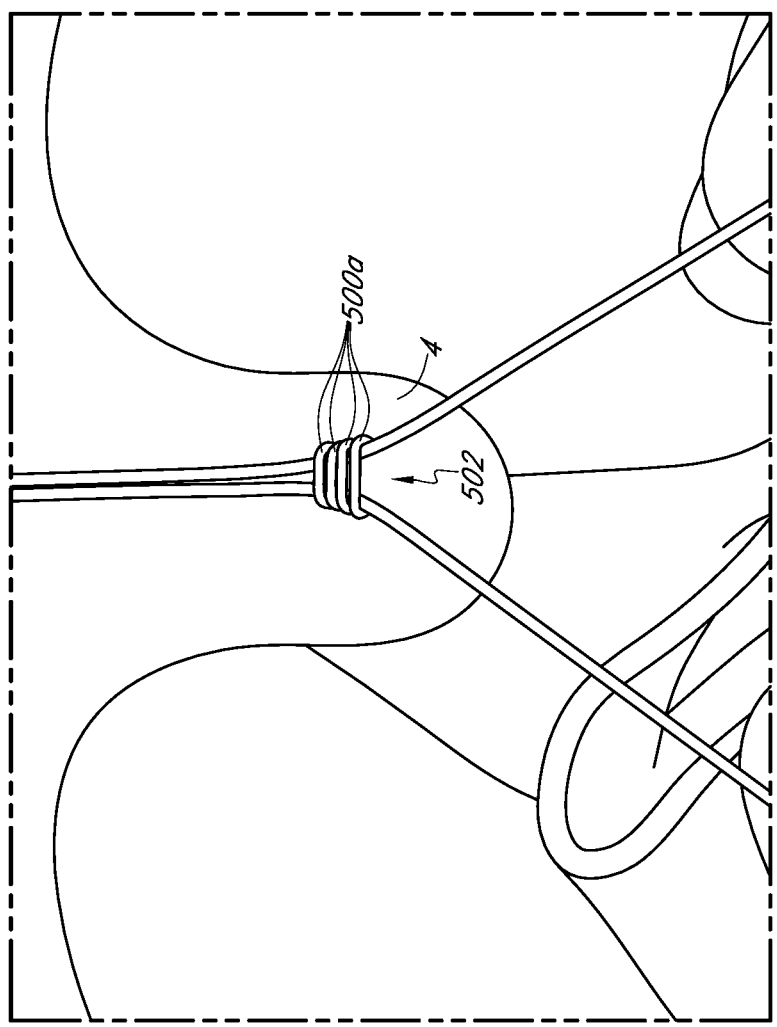
FIG. 14B shows a detail view of the suture routing of FIG. 14A.

As mentioned earlier, sutures are used to deploy or activate the valve holder and place the prosthetic valve in a deployed position where the commissure posts are urged radially inward toward a center of the valve to reduce or eliminate suture looping. Another aspect of the invention is the use of a suture loop or loops that straddle across each commissure post tip to assist with suture routing for placing the commissure posts in the deployed state. With reference to FIGS. 14A and 14B, suture loops 500 are attached to each commissure post 4 near the tip. The suture loops can be made of any suitable material, such as cloth or fabric, and can be stitched or otherwise attached to the commissure post. Several suture loops 500a may be attached adjacent each other to form a suture passage 502. Sutures are routed under the loops and thus avoid having to be pushed through multiple layers of cloth. Suture routing from the commissure posts 4 to the valve holder body 20 will now be described in detail.

In one method, suture routing is performed by knotting an end of a deployment suture 250, then taking the other end of the suture and routing it into the central opening 120 of the rotor 22 and through one of the holes 130 of the sidewall of the rotor 22 (see FIG. 10). The suture is pulled taut so that the knotted end rests in the central opening 120 and stops against the inside of the sidewall at the hole 130. The free end of the deployment suture is next fed through one of the openings 86 of the valve holder body 20. Two other deployment sutures are also routed through the other corresponding holes 130 of the rotor and openings 86 of the valve holder body 20.

Once the sutures are routed through the valve holder body 20, the rotor 22 can be fit into the central opening 50 of the valve holder body 20. Notably, in this position, the flexible arms 112 of the rotor have teeth 114 that engage the ratchet wall 80 of the valve holder body. This will provide a ratcheting mechanism that allows the rotor 22 to rotate in one direction and pull on the sutures. In addition, the bottom of the rotor protrudes beyond the bottom of the valve holder body to prevent suture entanglement among the sutures passing from the rotor through the valve holder body. Such entanglement could seize up the ratchet mechanism and prevent rotation and deployment. Preferably, when assembled, the rotor rib 124 is parallel to the suture mounts 32 of the valve holder body 20.

After the rotor 22 is assembled to the valve holder body 20, the guide body 24 can be snapped onto the rotor/holder body assembly. The snap arms 64 of the valve holder body 20 will deflect radially outwardly as the three stops 170, 176 are pressed against the snap arms 64, and the snap arms will snap back once the stops 170, 176 clear the ramped surfaces 72 of the snap arms to lock the guide body 24 to the valve holder body 20 (see FIG. 11). Assembly is easily performed by pushing all three stops against the snap arms at once, or by snapping in the larger first stop 170, followed by snapping in the two additional stops 176. Notably, the snap arms 64 point away from where the prosthetic heart valve is attached to the valve holder body reducing the possibility of damage to the new valve during assembly. If desired, the guide body may have a different color for more visible contrast and to assist in identifying the location of the cutting well iso.

With reference to FIGS. 2, 5B, and 14A, the inflow side 7 of the sewing ring 5 of the prosthetic heart valve 1 will be secured to the underside 91 of the rim 90 of the valve holder body 20. Prior to this, the free ends of the deployment sutures 250 (FIG. 10) from the rotor 22 will be routed through loops 500 on the commissure posts 4a, 4b, 4c. Accordingly, the free end of one suture 250a from the rotor and opening 86a of the valve holder body 20 is threaded through the sewing ring 5 from the inflow side (FIG. 14A). Preferably, the suture 250a is routed from directly under the center of the corresponding commissure posts 4a and threaded straight up through the sewing ring 5. The suture 250a is then routed along the outside of the cloth covering of the commissure post 4a and threaded under the loop or loops 500a at or near the tip of the commissure post 4a. A needle can be used to pass the suture 250a through the sewing ring and through the loops 500a.

After routing the suture 250a up the first commissure post 4a and under the loops 500a, the suture 250a is routed to the tip of an adjacent commissure post 4b and then threaded down through a corresponding loop or loops 500b on the adjacent commissure post 4b. Next, the suture 250a is routed down along the outside of the cloth covering of the commissure post 4b and through the sewing ring 5 at the base of commissure post 4b. When each of the three sutures are routed in this way, it results in pairs of sutures extending along each commissure post, i.e., sutures 250a, 250b on commissure post 4b, sutures 250c, 250a on commissure post 4a, etc. Preferably, the sutures of each pair are routed directly next to each other, or even touching, along the length of the commissure post and pass through the sewing ring 5 on either side of a thread forming the cloth-covering of the sewing ring.

Once the suture 250a is routed back to the inflow side of the sewing ring 5, the suture 250a is routed through a hole 42b in the rim 90 of the valve holder body 20 (FIG. 5c). A needle can be used to route the suture 250a through the loops 500b of the commissure post 4b, to press through the sewing ring 5 and pass through the platform hole 42b. Preferably, the hole 42b selected in the recessed area 40b is the hole farthest from the suture mounts 32. Similar routing is followed for sutures 250b and 250c. At this point, the needle from each suture can be removed. Preferably, suture routing through the commissure posts is counterclockwise when viewed from the outflow side of the valve (see routing of suture 250a in FIG. 14a).

This type of suture routing at the commissure posts of the prosthetic heart valve has benefits over previous techniques. Previously, the sutures were routed from the valve holder through the central outflow area and extended toward the commissure tips, passing through the coaptation area between the leaflets on the way. This routing seemed to be effective in preventing suture looping, but had two main issues—suture contact with the leaflets and high holder removal force. In the routing depicted in FIGS. 10 and 14A, the sutures 250 are routed from the central opening 120 of the valve holder body through the openings 86 and laterally toward the sewing ring, rather than at an angle toward the commissure tips. From there, each suture passes through the sewing ring, through suture loops 500 near the commissure tip, toward the next commissure tip, and then down that commissure, back through the sewing ring, and finally through the valve holder. The new routing is no more difficult to assemble, eliminates having to pass sutures through the tissue coaptation, and, owing to fewer and less drastic turns in the routing, results in a much lower holder removal force.

After the last suture 250c has been returned to the valve holder body 20 through one of holes 42a of the recessed area 40a, the suture 250c is routed back down through the platform rim 90 through the other hole 42a of the recessed area 40a. After that, the suture 250c is fed back up through tunnel hole 34, placed across the cutting well 150 of the guide body 24 using recesses 158, then through the tunnel of the other suture mount 32 (see FIG. 11). The suture 250a is routed in a similar way.

For suture 250b which has been fed up through hole 42c of the recessed area 40c located opposite from the cutting well 150, the suture 250b is routed back down through the other hole 42c in the same recessed area 40c. The suture 250b is then routed under the valve holder body 20 to the same hole 42a that suture 250C was routed. Suture 250b is then routed up through hole 42a, back down through the other hole 42a, then back up through tunnel hole 34, just like suture 250c. Suture 250b is then fed across the cutting well iso. Each suture is pulled to tighten and tied off on the closest suture mount 32. A holder fixture (not shown) that is known in the art may be used to assist in alignment of the commissure posts and suitable tightening of the sutures.

After the deployment sutures 250a, 250b, 250c have been routed and secured, a handle attachment suture 260 is used to secure the handle adapter 26 to the guide body 24. With reference to FIGS. 4, 7A, and 8A, the attachment suture 260 is threaded under one of the arms 152, 154 of the cutting well 150 of the guide body 24 at the location of the recess 156. The length of the thread is centered at the recess 156 and knotted around the arm. The handle adapter 26 is placed into the guide body 24 with the shield 216 facing the cutting well 150 of the guide body 24. Preferably, the lower tubular part 204 of the handle adapter rests on the platform 190 of the guide body, leaving a small gap 262 between the ledge 206 of the handle adapter and the top of the tubular wall 140 of the guide body. The gap 262 serves as a channel for attachment suture 260 in order to better hide or cover the exposed suture routing. The extension portions 209 of the ledge also assist in hiding the suture routing.

With the center of the suture 260 tied to one of the arms 152, 154 of the guide body 24, a first end portion of the suture 260 is routed under the other arm 152, 154, then routed up and back across the suture guard 210 of the handle adapter 26. The first end portion is received in the recesses 220 of the suture guard and is then routed in the gap 262 between the ledge 206 of the handle adapter and the top of the guide body 24 to the suture support 220. The first end portion is then routed to the other side of the suture support, up through the cutout 232, and down through hole 230 and knotted at that location leaving a tail. The second end portion 266 of the attachment suture 260 is routed the same way in the opposite direction. In a final step, one of the suture tails is threaded under the first stop 170 of the guide body and back up through a hole 230 of the handle adapter. The tail is located in the recess 174 of the first stop 170, is tightened, and is knotted with the other tail to the suture support 220. This improved suture tie-down better secures the handle adapter to the guide body and prevents unintentional separation during handling and implantation.

When the handle adapter 26 and the guide body 24 are secured together, the shield 216 of the handle adapter 26 provides an additional safety feature against inadvertent or premature release of the prosthetic valve from the valve holder 14. When the handle adapter 26 is coupled to the holder 14, the shield 216 is aligned with the cutting well 150 of the guide body 24, and is positioned over and covers the cutting well 150, thereby preventing or reducing inadvertent or unintended cutting or breaking of the sutures connecting the valve holder 14 to the prosthetic heart valve. When the handle adapter 26 is removed, the cutting well 150 is revealed and the suture or sutures connecting the valve holder 14 to the prosthetic valve can then be cut or untied to release the valve. In addition, assembly and disassembly of the handle adapter and the guide body is easily achieved by a simple axial movement between the parts, no tilting of the parts is needed.

Figure 7C:
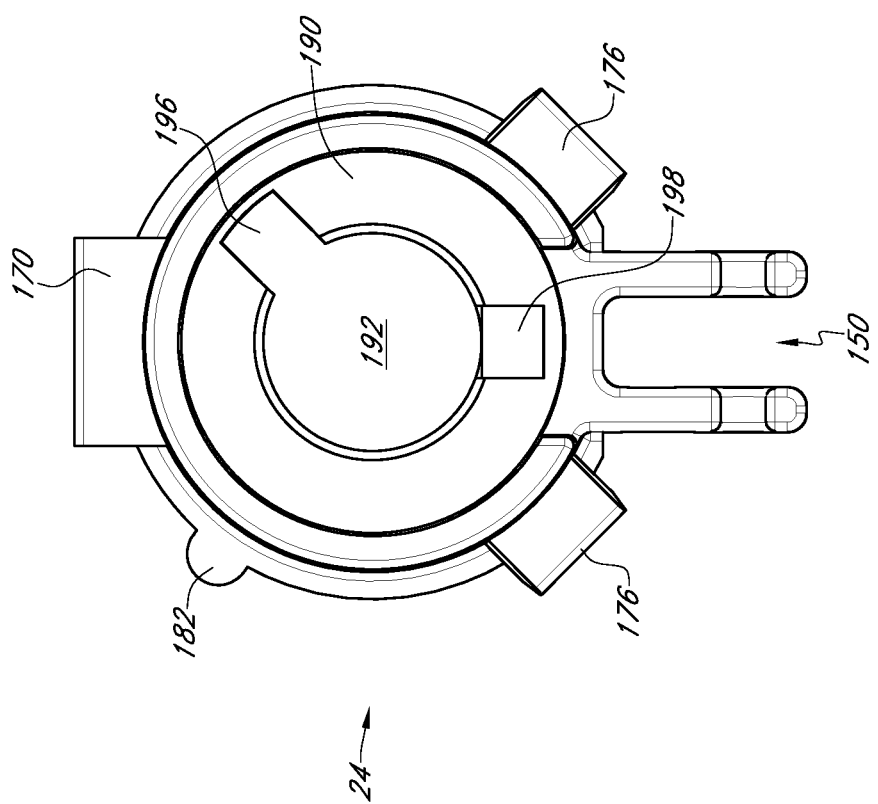
FIG. 7C shows a top view of the guide body of the heart valve implant holder assembly of FIG. 3.
Figure 8C:
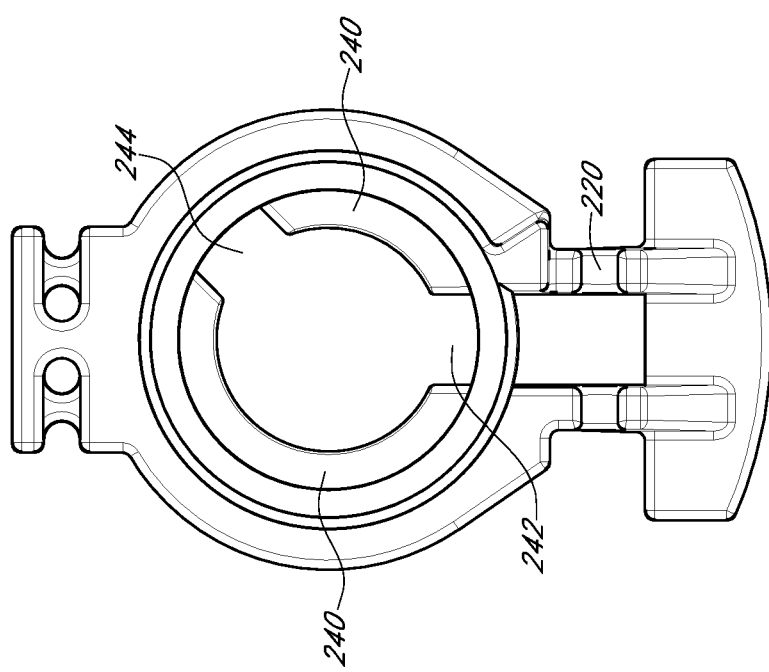
FIG. 8C shows a top view of the handle adapter of the heart valve implant holder assembly of FIG. 3.

With the valve holder 14 assembled, the activator dial 16 may be attached to deploy the commissure posts to a collapsed or bent configuration. The central shaft 302 of the dial 16 is inserted into the central bore 234 of the handle adapter 26 (FIG. 3). In particular, the flexible arm 310 of the dial 16 is aligned with the first alignment keyway 242 (FIG. 8c) of the handle adapter 26 and the ramp 198 of the guide body 24 (FIG. 7c). When inserted, the flexible arm 310 will pass through the first alignment keyway 242 and engage the ramp 198. The marker 330 on the upper surface 326 of the dial 16 assists in locating the proper orientation of the flexible arm 310 of the dial for assembly, where for example, a corresponding marker or other indicia may be present on another part of the valve holder 14 or other device the dial 16 is configured to connect to, to aid in proper alignment with marker 330 on dial 16 during insertion or attachment.

After passing through the handle adapter 26, the key 322 of the flexible arm 310 engages the ramp 198 of the guide body 24. Due to the flexibility of the flexible arm 310 of the dial 16, contact between the key 322 and the ramp 198 of the guide body 24 causes the flexible arm 310 to bend inwards into the central cavity of the dial 16 such that the key 322 may pass through the central bore 192 of the guide body 24. The lower surface of the key 322 has an oblique or slanted shape (e.g., via a chamfer or fillet) to facilitate inward bending of the flexible arm 310. Once the key 322 passes the central bore 192 of the guide body 24, the flexible arm 310 returns to its original unbent shape. An upper surface of the key 322 has a flat shape that matches an underside surface of the platform 190 to prevent or hinder the flexible arm 310 from bending once the key 322 passes the central bore 192 of the guide body 24. This is to retain the dial 16 in the guide body 24 and prevent inadvertent or unintended removal of the dial 16 before deployment of the valve holder 14 is complete. Recesses 324 at the bottom of the central shaft 302 provide accommodation space for the sutures and suture knots in the central opening 120 of the rotor 22. The spacers 346 of the dial 16 engage the central bore 234 of the handle adapter to provide a tighter fit and increased stability.

Once the key 322 passes the central bore 192 of the guide body 24 and the dial 16 is connected to the rotor 22, the dial 16 may be rotated to cause the rotor 22 to rotate and deploy the commissure posts. The sutures attached to the rotor are pulled and slide through the suture loops 500 to cause the commissure posts to fold inward. The rotor 22 has a one-way ratcheting mechanism such that the dial 16 may only be rotated in one direction, and the dial 16 is prevented from being rotated in an opposite direction. The underside of the guide body 24 has space to facilitate rotation of the dial 16 relative to guide body 24, which provides clearance for the key 322 of the dial 16 during rotation.

The dial 16 has an angled flange 338 that, together with the vertical rib 208 of the handle adapter 26, acts as a stop after the dial has been rotated to fully deploy the commissure posts. With reference to FIG. 4, the dial 16 is shown in a first position where the key 322 of the central shaft 302 has been aligned with the ramp 198 of the guide body 24, and the central shaft 302 of the dial is connected to the rotor 22. The dial marker 330 assists in locating the proper orientation. The dial 16 is then rotated clockwise (in the direction of the arrows) until the angled flange 338 stops against the vertical rib 208. The rotational movement is less than 360 degrees such that the dial 16 is restricted to less than one full rotation in use. The stop prevents over-deployment or over-tightening of the valve. The dial 16 may be removed by removing the key 322 upwards through the keyway 196 of the guide body 24 and through the second alignment keyway 244 of the handle adapter 26. Upon removal of the dial 16, the valve holder 14 is in the fully deployed configuration. In addition, the keyway 196 and the one-way ratcheting mechanism prevent under-deployment of the valve. The dial 16 is prevented or hindered from being removed from the guide body 24 until the key 322 is aligned with the keyway 196.

Figure 11:
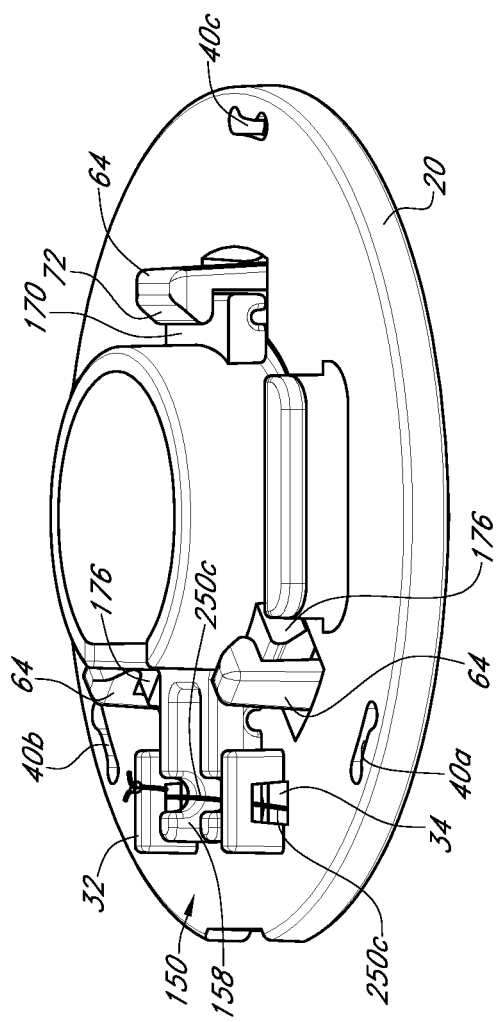
FIG. 11 shows a top perspective view of the assembled guide body and valve holder body of FIG. 4.
Figure 12A:
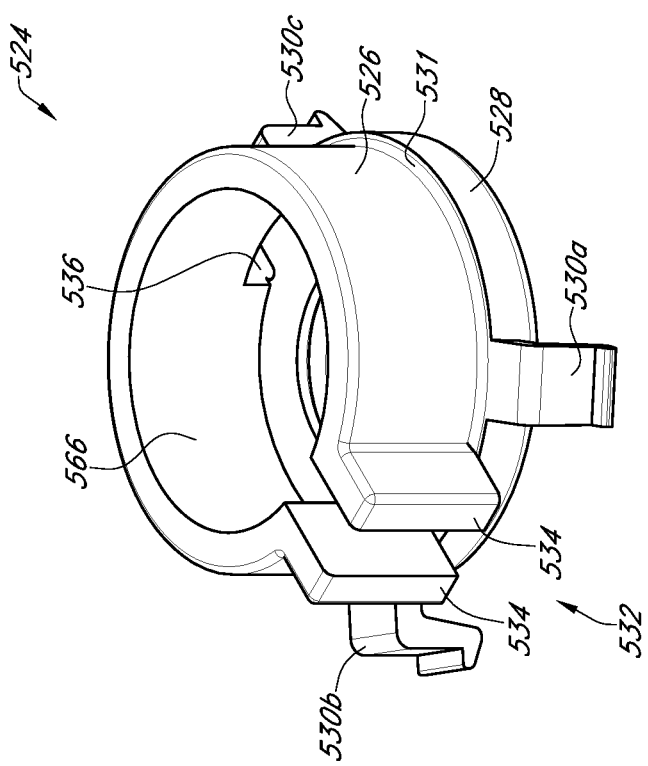
FIG. 12A shows a top perspective view of an alternative embodiment of a guide body of the heart valve implant holder assembly.
Figure 12B:
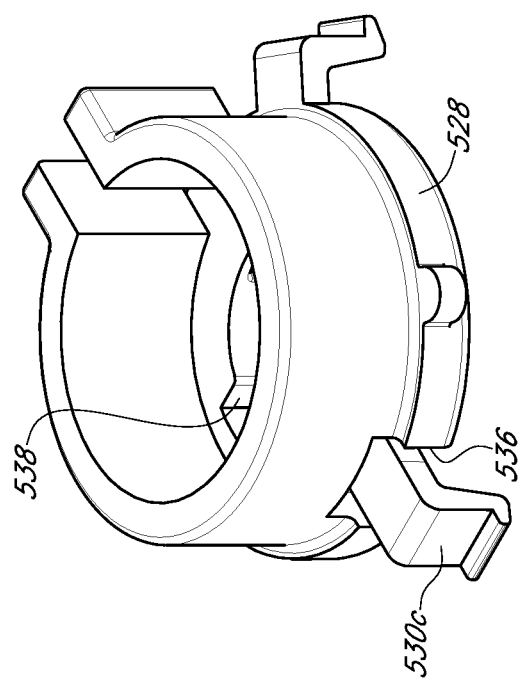
FIG. 12B shows a top perspective view of the guide body of FIG. 12A from the other side.
Figure 12C:
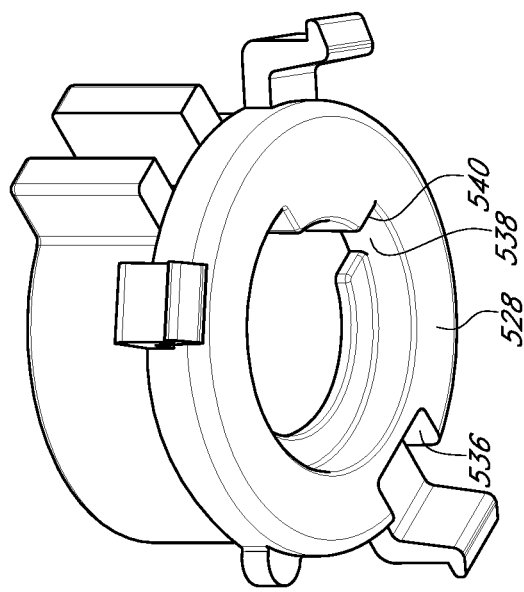
FIG. 12C shows a bottom perspective view of the guide body of FIG. 12A.

Upon removal of the dial 16, a handle (not shown) can be attached to deliver the prosthetic heart valve to the valve site. The handle is threaded to the screw thread 240 of the handle adapter 26. Once the prosthetic valve is secured to the valve site, the handle and the handle adapter 26 can be removed by cutting the handle attachment suture 260 at the recesses 220 of the suture mount 210 of the handle adapter. Alternatively, the handle by itself can be removed by unscrewing it. The suture 260 is tied off to the handle adapter and will be removed with the handle adapter. With the suture mount 210 of the handle adapter removed, the sutures 250 connecting the valve holder body 20 to the prosthetic valve are exposed (FIG. 11). The valve holder body 20, together with the guide body 24 and rotor 22, can now be removed from the prosthetic valve by cutting the sutures 250 at the single cut point of the cutting well 150.

Several variations to the above described assembly may be used. With reference to FIGS. 12A-12C and 13A-13B, an alternative guide body 524 and handle adapter 526 may be used. The guide body 524 is similar to the guide 306 described in U.S. Patent Application Publication 2018/0116755 and can be used with the valve holder body 302 disclosed in that publication. The guide body 524 has flexible arms 530 that snap into openings 320 of the valve holder body in the publication.

Similar to the first embodiment, the guide body 524 has an upper tubular wall 526 and a lower tubular wall 528 and a ledge 531 that separates the upper and lower walls. Along one side, the upper tubular wall 526 has an opening 532 and opposed flanges 534 that project from the wall 526 to define the opening 532. Two flexible arms 530a, 530b extend from the lower tubular wall 528 and are adjacent the opposed flanges, respectively.

On the opposite side from the opposed flanges, the guide body has a cutout 536 that extends partially into the lower tubular wall 528 and entirely through the upper tubular wall 526. A third flexible arm 530c is located in the cutout 536 and is cantilevered from the lower tubular wall 528 from a location inside the cutout 536. This results in a longer flexible arm 530c than the two flexible arms 530a,b and easier assembly to the valve holder body. Similar to the guide 306 in the aforementioned publication, the guide body 524 has a keyway 538 which provides a passage for removal of the activator dial 16 and a wall 540 which provides a stop that limits rotation of the dial, all described more fully in the publication.

Figure 13A:
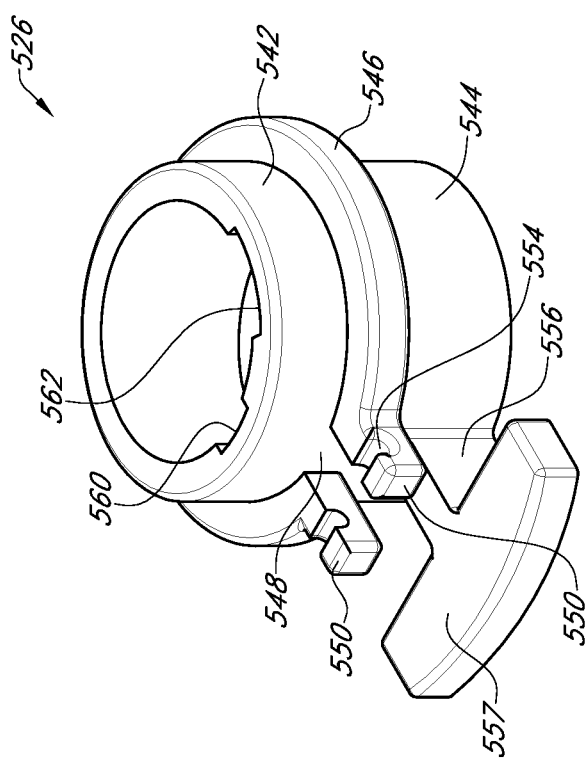
FIG. 13A shows a top perspective view of an alternative embodiment of a handle adapter of the heart valve implant holder assembly.
Figure 13B:
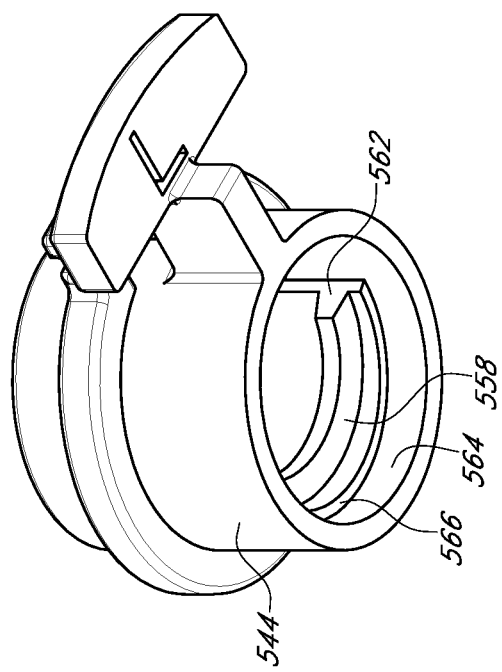
FIG. 13B shows a bottom perspective view of the handle adapter of FIG. 13A.

With referenced to FIGS. 13A and 13B, the handle adapter 526 is similar to the handle adapter 26 of the first embodiment. The handle adapter 526 is a cylindrical tube having an upper tubular part 542 and a lower tubular part 544. The lower tubular part is sized to fit inside the opening of the guide body 524. A ledge 546 is arranged around the cylindrical tube between the upper part 542 and the lower part 544. The ledge 546 has a recess 548 and, on each side of the recess, a support 550 extends from the ledge to form a suture mount. Each support has a notch 554 for a suture. Below the suture mount is a strut 556 extending from the lower tubular part 544. At the end of the strut 556 is a suture guard 557.

Inside the bore of the handle adapter 526 is a screw thread 558. The thread 558 has a first alignment keyway 560 and a second alignment keyway 562 to facilitate insertion and removal of the activator dial 16. The inner wall of the cylindrical tube is also recessed at the location of the keyways 560, 562. An inner wall 564 at the bottom of the lower tubular part 544 is also recessed and forms an undercut surface 566.

The handle adapter 526 is assembled to the guide body 524 by inserting the lower tubular part 544 into the central opening 566 of the guide body 524. The opening 532 between the opposed flanges 534 of the guide body 524 provides space for passage of the strut 556 of the handle adapter 526. The second alignment keyway 562 of the handle adapter is aligned with the keyway 538 of the guide body 524.

Figure 15B:
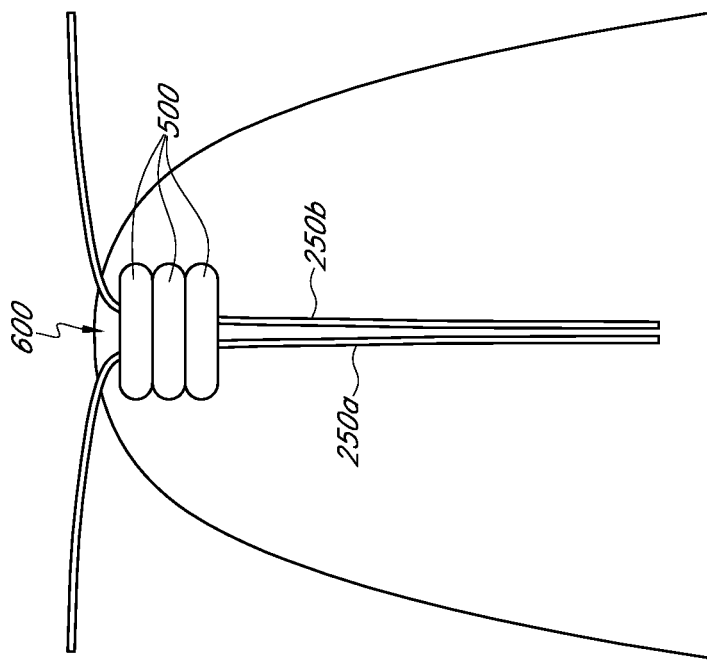
FIGS. 15A-15H shows several embodiments of suture loops and suture routings.
Figure 15A:
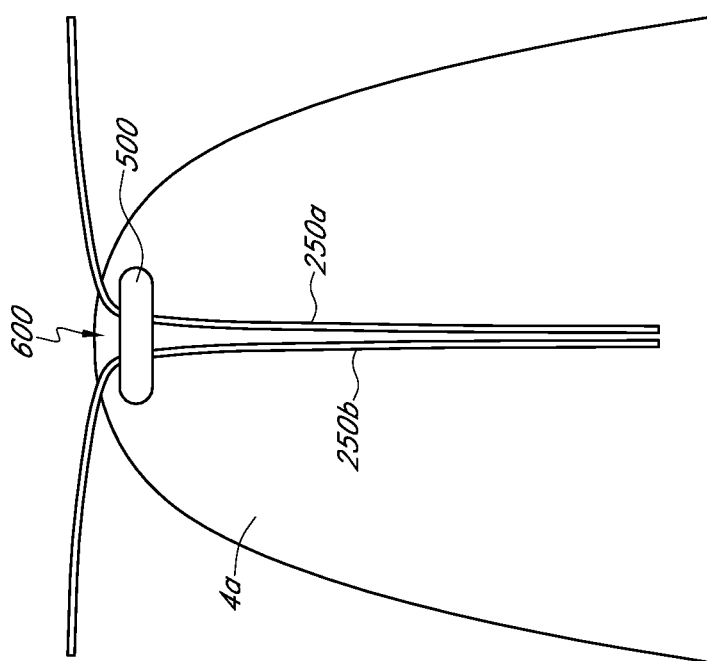
Figure 15D:
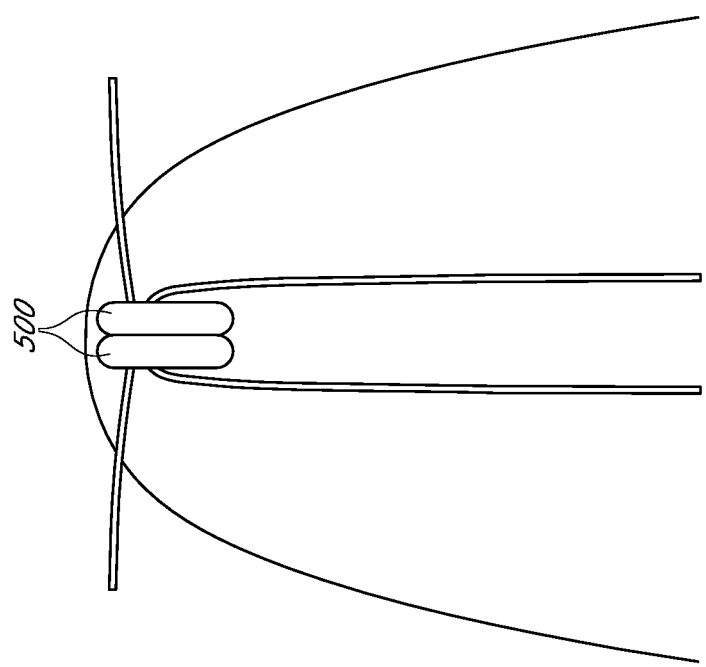
Figure 15C:
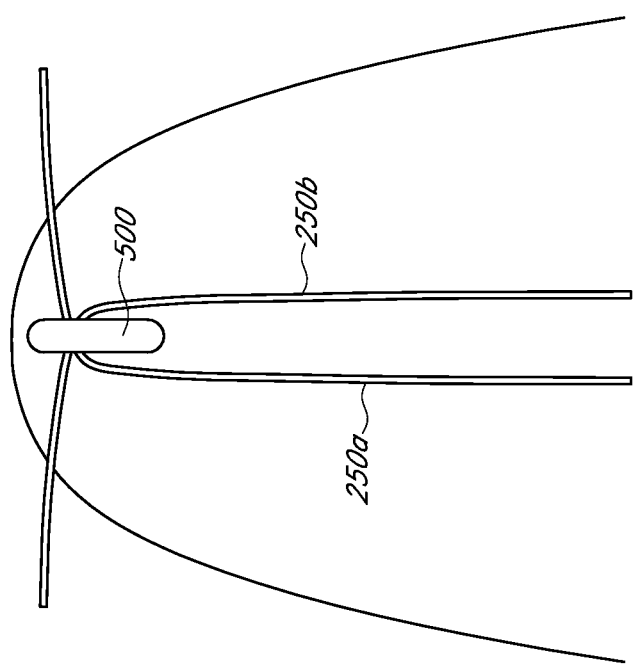
Figure 15F:
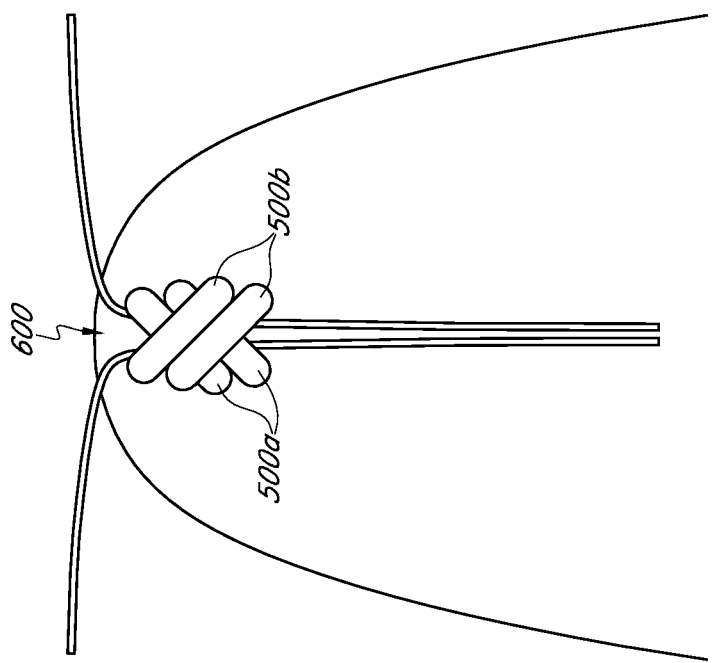
Figure 15E:
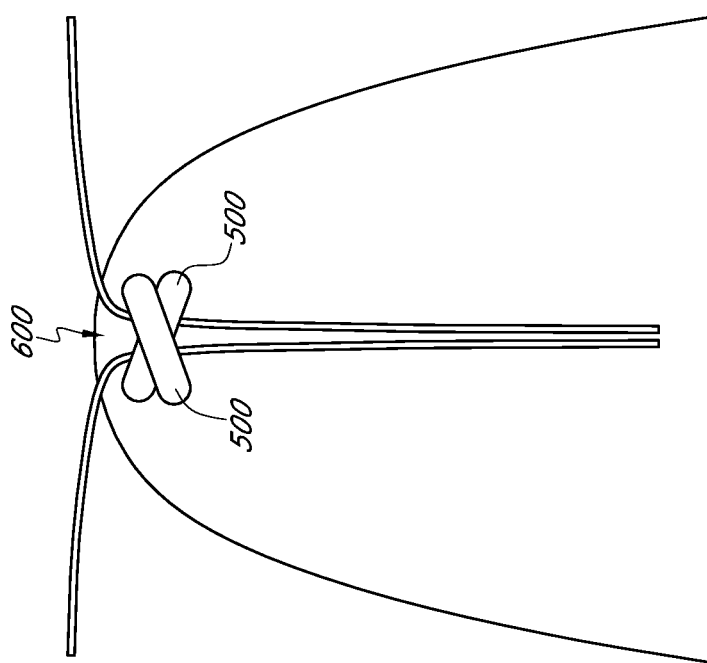
Figure 15H:
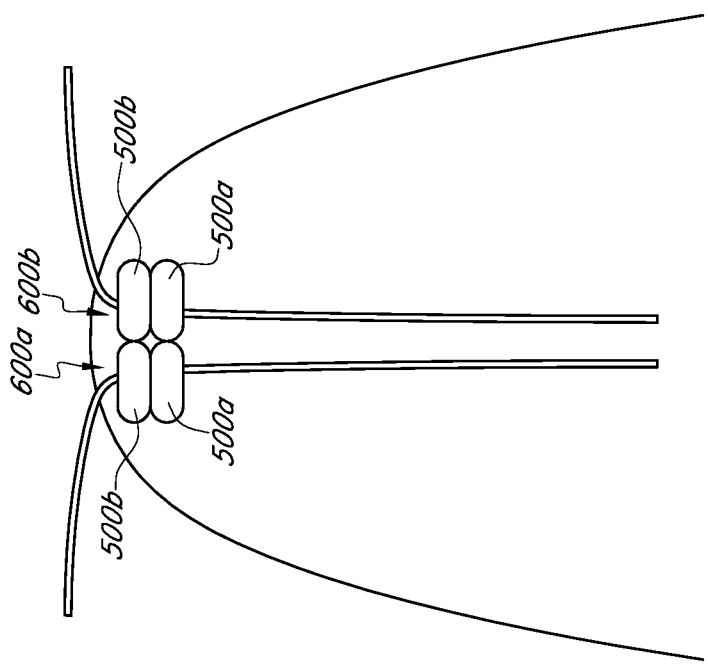
Figure 15G:
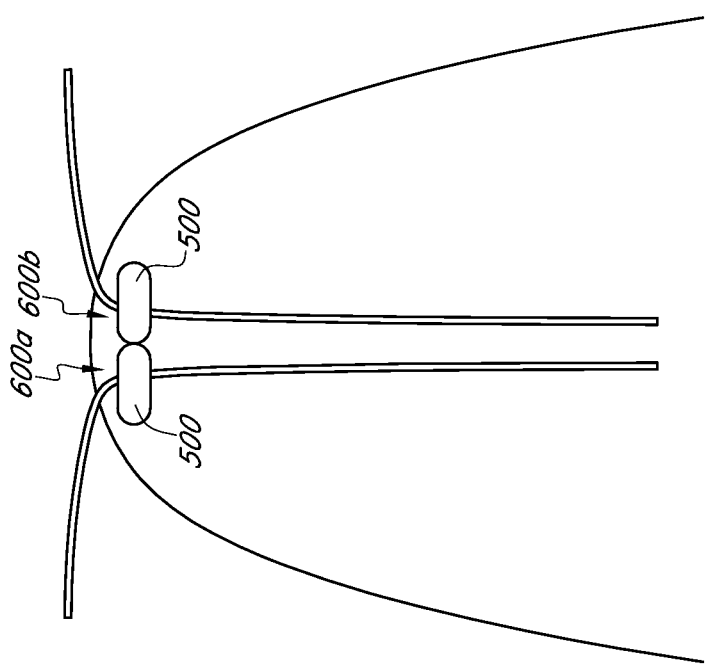

With referenced to FIGS. 15A-15H, several variations for attaching suture loops 500 to commissure posts 4 and routing sutures 250 through the suture loops are provided. FIG. 15A provides a single suture loop 500 for both sutures 250a, 250b. FIG. 15B provides three suture loops 500 a, b, c that provide a single passage 600 for both sutures 250a, 250b. FIG. 15C provides a single suture loop 500 aligned vertically and the sutures 250a, 250b cross over each other. FIG. 15D provides two vertical loops 500 and crossover sutures. FIG. 15E provides overlapping loops 500 and a single vertical passage 600. FIG. 15F provides multiple pairs of overlapping loops 500a, 500b and a single vertical passage. The overlapping loops may also be arranged to provide a single horizontal passage (not shown). FIG. 15G provides two end-to-end horizontally arranged loops 500 with separate passages 600a, 600b for the sutures. FIG. 15H provides one pair of end to end horizontally arranged suture loops 500a above another pair of similarly arranged loops 500b resulting in separate vertical passages 600a, 600b for the sutures. The arrangements in FIGS. 15G and 15H can be rotated 90 degrees to provide horizontal passages if desired.

In other alternative embodiments, various different features from the different embodiments discussed herein and incorporated by reference can be combined in a single modified heart valve implant holder assembly.

For purposes of this description, certain aspects, advantages, and novel features of the embodiments of this disclosure are described herein. The disclosed methods, apparatus, and systems should not be construed as being limiting in any way. Instead, the present disclosure is directed toward all features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods.

What is claimed is:

1. A heart valve and valve holder assembly comprising:
   a prosthetic heart valve comprising a plurality of valve leaflets that control directional flow of blood through a heart, a stent structure having a plurality of flexible commissure posts supporting the valve leaflets, the stent structure having a fabric covering over the plurality of commissure posts and having a sewing ring at an inflow end of the stent structure, each of the plurality of commissure posts having a tip and a first suture loop attached to the fabric covering at a location adjacent to or on the tip of the commissure post, wherein each first suture loop provides a passage for a suture to pass through between the fabric covering and the suture loop;
   a valve holder, comprising:
      a valve holder body to hold a prosthetic heart valve, the valve holder body having an upper surface, a bottom surface shaped to abut an inflow side of the prosthetic heart valve, and a central axis;
      a rotor insertable through the upper surface and positioned in the valve holder body, wherein when the prosthetic heart valve is coupled to the valve holder body, the rotor is rotatable around the central axis to adjust the prosthetic heart valve to a delivery position;
      a guide body mounted to the valve holder body and projecting above the upper surface of the valve holder body when assembled, the guide body having an opening through which an activator is couplable to the rotor for rotating the rotor around the central axis of the valve holder body;
      a handle adapter insertable into the opening of the guide body along the central axis, the handle adapter having an opening through which the activator is couplable to the rotor for rotating the rotor around the central axis of the valve holder body, the opening of the handle adapter also configured to receive a handle, and
   deployment sutures connecting the valve holder to the prosthetic heart valve, each deployment suture being attached to the rotor, routed through the passage of a first suture loop on one of the commissure posts, and back to be tied off on the valve holder such that rotation of the rotor creates tension in each deployment suture to deflect each commissure post radially inward and adjust the prosthetic heart valve to the delivery position.

2. The assembly of claim 1, wherein each deployment suture is attached to the valve holder, routed through the sewing ring, through the first suture loop of a first commissure post, through the first suture loop of a second commissure post, again through the sewing ring, and back to the valve holder.

3. The assembly of claim 1, wherein the passage of each first suture loop is aligned with the tip of the commissure post.

4. The assembly of claim 1, wherein the passage of each first suture loop is aligned perpendicular to the tip of the commissure post.

5. The assembly of claim 1, wherein each commissure post has an additional suture loop or loops attached to the fabric covering at a location adjacent to or on the tip of the commissure post, wherein the first suture loop and the additional suture loop or loops are aligned to provide a single aligned passage for a suture to pass through between the fabric covering and the suture loops.

6. The assembly of claim 1, wherein each commissure post has an additional suture loop attached to the fabric covering at a location adjacent to or on the tip of the commissure post, wherein the first suture loop and the additional suture loop are located end to end to provide two adjacent passages for a suture or sutures to pass through between the fabric covering and the suture loops.

7. The assembly of claim 1, wherein the activator has an activator dial and a central shaft connectable to the rotor for rotating the rotor around the central axis of the body.

8. The assembly of claim 7, wherein the deployment sutures cross over a cutting well on the guide body before being tied off on the valve holder, and the activator dial is large enough to cover the cutting well so as to require removal of the activator before the deployment sutures can be severed to detach the valve holder from the prosthetic heart valve.

9. The assembly of claim 1, wherein the handle adapter is secured to the guide body with a handle attachment suture, and the handle adapter has a shield that covers the cutting well so as to require removal of the handle adapter before the deployment sutures may be severed to detach the valve holder from the prosthetic heart valve.

10. The assembly of claim 9, wherein the opening of the handle adapter has threading configured to receive mating threading on a handle.

11. A heart valve and valve holder assembly comprising:
a prosthetic heart valve comprising three valve leaflets that control directional flow of blood through a heart, a stent structure having three flexible commissure posts supporting the valve leaflets, the stent structure having a fabric covering over the plurality of commissure posts and having a sewing ring at an inflow end of the stent structure, each of the commissure posts having a tip and a first suture loop attached to the fabric covering at a location adjacent to or on the tip of the commissure post, wherein each first suture loop provides a passage for a suture to pass through between the fabric covering and the suture loop;
a valve holder, comprising:
a valve holder body to hold a prosthetic heart valve, the valve holder body having an upper surface, a bottom surface shaped to abut an inflow side of the prosthetic heart valve, and a central axis;
a rotor positioned in the valve holder body, wherein when the prosthetic heart valve is coupled to the valve holder body, an activator is couplable to the rotor for rotating the rotor around the central axis to adjust the prosthetic heart valve to a delivery position;
three deployment sutures connecting the valve holder to the prosthetic heart valve, each deployment suture being attached to the rotor, routed through the passage of a first suture loop on one of the commissure posts, and back to be tied off on the valve holder such that rotation of the rotor creates tension in each deployment suture to deflect each commissure post radially inward and adjust the prosthetic heart valve to the delivery position.

12. The assembly of claim 11, wherein each deployment suture is attached to the valve holder, routed through the sewing ring, through the first suture loop of a first commissure post, through the first suture loop of a second commissure post, again through the sewing ring, and back to the valve holder.

13. The assembly of claim 11, wherein the passage of each first suture loop is aligned with the tip of the commissure post.

14. The assembly of claim 11, wherein the passage of each first suture loop is aligned perpendicular to the tip of the commissure post.

15. The assembly of claim 11, wherein each commissure post has an additional suture loop or loops attached to the fabric covering at a location adjacent to or on the tip of the commissure post, wherein the first suture loop and the additional suture loop or loops are aligned to provide a single aligned passage for a suture to pass through between the fabric covering and the suture loops.

16. The assembly of claim 11, wherein each commissure post has an additional suture loop attached to the fabric covering at a location adjacent to or on the tip of the commissure post, wherein the first suture loop and the additional suture loop are located end to end to provide two adjacent passages for a suture or sutures to pass through between the fabric covering and the suture loops.

17. The assembly of claim 11, wherein the activator has an activator dial and a central shaft connectable to the rotor for rotating the rotor around the central axis of the body.

18. The assembly of claim 17, wherein the deployment sutures cross over a cutting well on the valve holder before being tied off on the valve holder, and the activator dial is large enough to cover the cutting well so as to require removal of the activator before the deployment sutures can be severed to detach the valve holder from the prosthetic heart valve.

19. The assembly of claim 11, wherein the valve holder further includes:
a guide body mounted to the valve holder body and projecting above the upper surface of the valve holder body when assembled, the guide body having an opening through which the activator is couplable to the rotor; and
a handle adapter insertable into the opening of the guide body along the central axis, the handle adapter having an opening through which the activator is couplable to the rotor, the opening of the handle adapter also configured to receive a handle.

20. The assembly of claim 11, wherein the handle adapter is secured to the guide body with a handle attachment suture, and the handle adapter has a shield that covers the cutting well so as to require removal of the handle adapter before the deployment sutures may be severed to detach the valve holder from the prosthetic heart valve.

* * * * *